(12) United States Patent
Chen et al.

(10) Patent No.: US 10,829,517 B2
(45) Date of Patent: Nov. 10, 2020

(54) METHOD FOR TREATING OR/AND PREVENTING CALCIUM DEFICIENCY-RELATED DISEASES

(71) Applicant: National Chung Hsing University, Taichung (TW)

(72) Inventors: Chuan-Mu Chen, Taichung (TW); Hsiao-Ling Chen, Changhua County (TW)

(73) Assignee: NATIONAL CHUNG HSING UNIVERSITY, Taichung (TW)

( * ) Notice: Subject to any disclaimer, the term of this patent is extended or adjusted under 35 U.S.C. 154(b) by 0 days.

(21) Appl. No.: 16/190,537

(22) Filed: Nov. 14, 2018

(65) Prior Publication Data

US 2019/0144502 A1 May 16, 2019

(30) Foreign Application Priority Data

Nov. 16, 2017 (TW) .............................. 106139796 A

(51) Int. Cl.
| | | |
|---|---|---|
| *A61K 38/10* | (2006.01) | |
| *C07K 7/08* | (2006.01) | |
| *A61K 38/03* | (2006.01) | |
| *A61P 19/10* | (2006.01) | |
| *A61P 3/14* | (2006.01) | |
| *A23L 33/17* | (2016.01) | |

(52) U.S. Cl.
CPC ................ *C07K 7/08* (2013.01); *A23L 33/17* (2016.08); *A61K 38/03* (2013.01); *A61K 38/10* (2013.01); *A61P 3/14* (2018.01); *A61P 19/10* (2018.01)

(58) Field of Classification Search
None
See application file for complete search history.

(56) References Cited

FOREIGN PATENT DOCUMENTS

WO    WO-2005081628 A2 *  9/2005   ......... C07K 14/4732

* cited by examiner

*Primary Examiner* — Xiaozhen Xie
(74) *Attorney, Agent, or Firm* — Muncy, Geissler, Olds & Lowe, P.C.

(57) ABSTRACT

The present invention discloses a method for treating or/and preventing calcium deficiency-related diseases, which comprises administering a composition containing an effective amount of a peptide to a subject, wherein the peptide has an amino acid sequence as shown in SEQ ID NO. 3. The calcium ions are allowed to bind to the peptide and enter the cells of the patient, to achieve the effect of treating or/and preventing calcium deficiency-related diseases.

7 Claims, 23 Drawing Sheets

Specification includes a Sequence Listing.

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
```

```
<223> OTHER INFORMATION: synthesis

<400> SEQUENCE: 1

Thr Glu Val Pro Ala Ile Asn Thr Ile Ala Ser Ala Glu Pro Thr Val
1               5                   10                  15

His

<210> SEQ ID NO 2
<211> LENGTH: 12
<212> TYPE: PRT
<213> ORGANISM: Artificial Sequence
<220> FEATURE:
<223> OTHER INFORMATION: synthesis

<400> SEQUENCE: 2

Thr Glu Val Pro Ala Ile Asn Thr Ile Ala Ser Ala
1               5                   10

<210> SEQ ID NO 3
<211> LENGTH: 6
<212> TYPE: PRT
<213> ORGANISM: Artificial Sequence
<220> FEATURE:
<223> OTHER INFORMATION: synthesis

<400> SEQUENCE: 3

Ile Asn Thr Ile Ala Ser
1               5
```

METHOD FOR TREATING OR/AND PREVENTING CALCIUM DEFICIENCY-RELATED DISEASES

BACKGROUND OF THE INVENTION

1. Field of the Invention

The present invention relates to a peptide-containing composition and use thereof, and particularly to a method for treating or/and preventing calcium deficiency-related diseases.

2. Description of the Related Art

The bone density of humans begins to decline year by year at the age of 30. In particular, postmenopausal women or men over 65 years of age are at high risk of suffering from osteoporosis. According to a health survey conducted in Taiwan from 2013 to 2015, 12.3% of the population suffers from osteoporosis, where the proportion of the patient increases with increasing age, and the proportion of women suffering from osteoporosis is significantly higher than that of men.

Osteoporosis refers to the formation of many voids in the bone, causing the bone structure to be hollow, thin and brittle. It may cause spinal compression fractures, hunchback, shortened height, or the occurrence of bone fractures and bone fragmentation when the patient experiences collision by an external force or falls down. For most of elderly people who suffer from osteoporosis, once hip fracture occurs, they often have to stay in bed for a long period of time or to be cared for by others because of the difficulty in healing, so that the family and society need to pay huge costs and medical resources. Moreover, according to statistics, about 200 of the patients with hip fractures die within a year.

In the past, it was thought that high intake of calcium could promote the supplementation of calcium in the body, so various kinds of calcium supplements became available. However, in fact, the absorption of calcium ions by the intestine depends on many external factors, such as daily intake of calcium or other nutrients, such as phosphoric acid, and phytic acid, etc., and internal factors, such as gastric acid secretion. Therefore, the body's calcium intake from the outside cannot be completely directly absorbed by the intestinal tract and utilized.

Although studies have indicated that simultaneous intake of calcium and vitamin D allows for the effective supplementation of calcium. Sun exposure can be affected by the skin color, lifestyle, climate, and geographical location, etc., which hinders the synthesis of vitamin D. For example, the melanin in the skin blocks UV rays and thus hinders the synthesis of vitamin D. Long sleeves, long pants or dark garments block UV rays and reduce the ability of the skin to synthesize vitamin D, and excessive sun exposure may also cause skin damage. In other words, even if a large amount of calcium is supplemented, if no enough vitamin D is synthesized in the body, the calcium cannot be absorbed and utilized by the body.

Currently, there are clinically available drugs for treating osteoporosis, including calcitonin, hormone therapy, bisphosphonate, and parathyroid hormone, etc. However, the above drugs are restricted to patients diagnosed with osteoporosis. That is, if the degree of bone loss does not reach the standard of osteoporosis, these drugs cannot be used. Moreover, long-term use of bisphosphonate drugs may cause the side effect, osteonecrosis of the jaw.

It can be seen from the above description that there is currently a need for a composition that can effectively treat or/and prevent osteoporosis-related disorders and has no side effects.

SUMMARY OF THE INVENTION

The main object of the present invention is to provide a method for treating or/and preventing calcium deficiency-related diseases, which comprises administering a composition containing an effective amount of a peptide to a subject, where the peptide has an amino acid sequence as shown in SEQ ID NO. 3.

The calcium deficiency-related diseases include osteoporosis and complications thereof, bond fractures, and others.

The peptide has the ability to promote cellular absorption of calcium ions, reduce intracellular oxidative stress, inhibit inflammation-related cytokines, inhibit the functions of osteoclasts, and enhance the proliferation and differentiation of osteoblasts, and thus can be used as an active ingredient in the composition to achieve the efficacy of preventing or/and treating diseases.

In an embodiment of the present invention, the peptide has an amino acid sequence as shown in SEQ ID NO. 1, SEQ ID NO. 2, or SEQ ID NO. 3.

In another embodiment of the present invention, the peptide has a homologous amino acid sequence that is 90% or more similar to SEQ ID NO. 1.

In another embodiment of the present invention, the peptide has a homologous amino acid sequence that is 90% or more similar to SEQ ID NO. 2.

In an embodiment of the present invention, the composition may be prepared into various forms, for example, the composition may be a pharmaceutical product, a nutritional supplement or a functional food, and the composition may be prepared to have any forms, types, and tastes.

When the composition is a pharmaceutical product, the composition comprises an effective amount of the peptide and at least a pharmaceutically acceptable carrier for the purpose of preventing or treating calcium deficiency-related diseases.

When the composition is a nutritional supplement or a functional food, the absorption efficiency of calcium ions from a diet can be enhanced in a subject, and calcium deficiency-related diseases, osteoporosis-related diseases, and inflammatory diseases can be treated or/and prevented by administering the composition to the subject.

Still further, since the peptide not only has the effect of promoting calcium absorption, but also inhibits the functions of osteoclasts and enhances the proliferation of osteoblasts, the composition is a calcium ion absorption promoter, a bone loss inhibitor or a bone growth promoter.

DETAILED DESCRIPTION OF THE PREFERRED EMBODIMENTS

Figure 1:
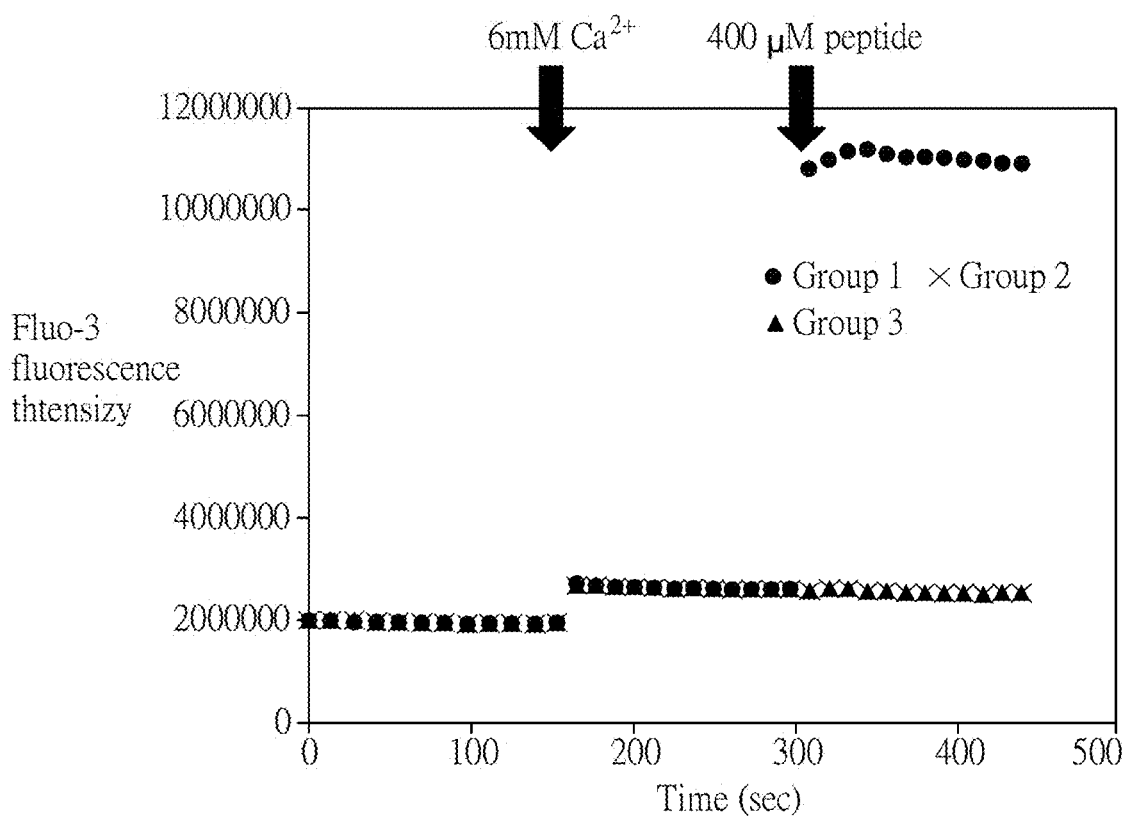
FIG. 1 shows the changes in fluorescence intensity of each group of Caco-2 cells treated under different conditions.

The novel peptide disclosed in the present invention has an amino acid sequence as shown in SEQ ID No. 3 (IN-TIAS), for example, the amino acid sequence of the novel peptide is as shown in SEQ ID No. 1, SEQ ID No. 2, or SEQ ID No. 3, or a homologous amino acid sequence that is 90% or more similarity to SEQ ID No. 1, or a homologous amino acid that is 90% or more similar to SEQ ID No. 2. The novel peptide can be obtained by extraction, fermentation, hydrolysis, artificial synthesis, a recombinant organism production platform or a combination of any two or more of the above methods.

The "homologous amino acid sequence" refers to an amino acid sequence derived by substituting, deleting or adding one or more amino acids in the amino acid sequence of a polypeptide.

The term "extraction" refers to a method in which a substance is separated from a mixture by taking advantage of the differences of the substance in different solvents, where the mixture from which the novel peptide of the present invention is obtained is derived from plants or animals, without limitation. Further, the techniques for separation or/and purification include, but are not limited to, separation of a specific size of a polypeptide by protein electrophoresis, liquid chromatography, separation using membranes of different sizes, and so on. These techniques are well known to those of ordinary skill in the art to which the present invention pertains, and thus are not described in detail herein.

The term "fermentation" refers to a method in which different metabolites such as a peptide, and an amino acid, etc are obtained through a fermentation reaction of a plant, an animal or a derivative thereof by a microorganism, and then a specific metabolite is further obtained by a technique of separation and purification. For example, the soybean contains a plurality of biologically active peptides after fermentation.

The term "hydrolysis" refers to a method in which plants, animals or their derivatives are hydrolyzed by enzymes or acids to produce specific peptides. For example, casein phosphopeptides is produced by hydrolyzing casein by trypsin or trypsase.

The term "artificial synthesis" refers to a method in which the amino acids are sequentially linked into a polypeptide, and which usually has the advantages of conveniences to change the primary structure of the polypeptide in the synthesis process, add a special amino acid, and modify the end of the polypeptide.

Furthermore, the artificial synthesis includes chemical synthesis and a peptide synthesizer. The chemical synthesis includes solid-phase peptide synthesis and liquid-phase peptide synthesis, where in the liquid-phase synthesis, an extraction operation is needed after completion of the linkage of each amino acid. However, since the polypeptide intermediate obtained by extraction is usually a mixture, a chromatographic purification step is still required. Therefore, the synthesis of polypeptides by liquid-phase synthesis involves complicated extraction and chromatographic purification steps to obtain a high-purity product.

The solid-phase synthesis includes a bonding reaction of a peptide on a solid polymer particle (or a polymer support). In this method, the N-terminal amino acid of a desired polypeptide is covalently bonded to a polymer particle, and then the subsequent amino acids are sequentially linked by means of specific bonding, to finally synthesize a polypeptide. Since the polymer particle is not soluble in the solvent, the polymer particle (and the desired polypeptide attached to the polymer particle) can be separated from the reaction agents and byproducts only by the washing and filtering operations after the reaction. Therefore, the solid-phase peptide synthesis not only has a higher yield but also can greatly shorten the reaction time because it does not require purification of the intermediate product, is also advantageous for the synthesis of long-chain polypeptides, and is currently a widely used peptide synthesis method.

The term "recombinant organism production platform" refers to the construction of a nucleic acid expressing a specific protein on an expression vector by a biotechnology, followed by transforming the recombinant expression vector into a host cell, such as *Escherichia coli*, yeast, *lactobacillus* or others, whereby the recombinant expression vector can express the nucleic acid in the host cell, thus obtaining the specific protein.

The term "effective amount" refers to the amount of a compound or an active ingredient required to produce a desired effect, which is expressed as a percentage by weight of the composition. As will be appreciated by those of ordinary skill in the art to which the present invention pertains, the effective amount will vary depending on the route of administration via which the particular effect is to be elicited. Generally, the active ingredient or compound may be present in the composition in an amount of from about 1% to about 100%, preferably from about 30% to about 100% by weight of the composition.

The term "pharmaceutical product" refers to that comprising an effective amount of a desired compound or active ingredient to produce a particular effect, and at least a pharmaceutically acceptable carrier. As will be appreciated by those of ordinary skill in the art to which the present invention pertains, the form of the pharmaceutical composition will vary depending on the route of administration via which the particular effect is to be elicited, for example, tablets, powders, injections, and the like, and the carrier may be a solid, a semi-solid or a liquid depending on the form of the pharmaceutical composition. For example, the carrier includes, but is not limited to, gelatin, emulsifiers, hydrocarbon mixtures, water, glycerin, physiological saline, buffered physiological saline, lanolin, paraffin, beeswax, dimethicone, and ethanol.

The term "calcium deficiency-related diseases" refers to disorders caused by low calcium ion concentrations in the body, such as cramps, high blood pressure, stroke, osteoporosis, fractures, brittle nails, brittle teeth, shoulder, neck and back pain, insomnia, and dizziness, etc.

The term "inflammatory reactions" refers to those induced by increased in-vivo expression of proinflammatory factors in vivo, such as IL-1, IL-6, TNF-α, and the like. In general, the inflammatory reactions can cause Alzheimer's disease, rheumatoid arthritis, osteoporosis, lupus erythematosus, hay fever, allergies, chronic arthritis and other diseases.

The word "a/an" or "the" used in the context of the present specification and claims is meant to include one or more referents, unless otherwise indicated.

Hereinafter, in order to further clarify the functions of the present invention, the present invention will be described in detail by way of examples. However, the examples are intended to be illustrative, and any words and phrases used herein are not intended to limit the invention and the scope and significance of the claims.

It should be noted that the animals in the following examples are bred and cared for in accordance with the requirements of the National Animal Center of the National Institute of Experimental Research (Guide for the care and use of Laboratory Animals), and the relevant experiments pass through the examination of National Chung Hsing University (IACUC No: 104-091).

The "Caco-2 cell line" used in the following examples is the abbreviation for human epithelial colorectal cancer cells, which enables the transport ability of the small intestine and is considered to be a good model for evaluating the intestinal transport mechanism, and thus is currently the most widely used cells to evaluate the calcium absorption in human intestine in medical experiments.

The "animal model of osteoporosis" used in the following examples is an Akr1A1 gene deficient mouse, which is unable to synthesize vitamin C in a large amount by itself, which may cause severe osteoporosis and oxidative stress imbalance. If the mouse is given vitamin C, the bone structure of the mouse can be restored to a nearly normal state.

The "vitamin C" used in the following examples is an antioxidant that reduces the damage of reactive oxygen species to osteoblasts, reduces inflammatory factors in the body, and inhibits the differentiation and activation of osteoclasts. The vitamin C has been disclosed in literatures to regulate the differentiation of chondrocytes by inhibiting ERK activation, and to induce the differentiation and activation of osteoblasts. In addition, studies have shown that the administration of vitamin C to ovariectomized female rats can increase the bone density and increase the in-vivo activity of the antioxidant enzymes superoxide dismutase and catalase in the body.

The statistical analysis methods for the results of the following examples are One-Way ANOVA and Duncan's post-hoc test. When the p value is less than 0.05, the result is considered to be statistically significant.

Example 1: Preparation of Peptide

A peptide having an amino acid sequence as shown in SEQ ID No. 1 was prepared by artificial synthesis, and the peptide sequence was confirmed to be TEVPAINTIASAEPTVH.

Example II: Culture of Caco-2 Cell Line

The Caco-2 cell monolayer was cultured in a 10 cm2 culture dish containing DEME medium, and the cells were separated by TrypLE (Invitrogen, Carlsbad, Calif.) and washed several times with a phosphate-free KRH (Krebs Ringer Heps) solution. 5 µL of 1 mM Fluo-3-AM dye and 20% (w/v) thermally reversible hydrogel (Pluronic F-127, RF127) solution were added at 37° C. for about 30 minutes to obtain a Caco-2 cell suspension. The KRH solution was prepared with 140 mM sodium chloride, 5 mM potassium chloride, 6 mM glucose, 10 mM HEPES, and 0.55 mM magnesium chloride and had a pH of about 7.4, and the thermally reversible hydrogel solution was formulated with thermally reversible hydrogel and 5 ml of the KRH solution.

The Caco-2 cell suspension containing Fluo-3-AM dye was thoroughly rinsed in phosphate-free KRH solution and aliquoted, each aliquot containing 5×107 cells. After each aliquot was pelletized, the cells were resuspended in 240 µL of the phosphate-free KRH solution, and then transferred to a 96-well plate for use.

Example 3: Cell Assay (I)

The Fluo-3-AM containing Caco-2 cell suspension was divided into three groups, and 6 mM calcium ions were added respectively at the 154th second. Then, at the 320th second, each group of cells was treated under the following conditions: 400 µM of the peptide of SEQ ID No. 1 of the present invention was added to the first group, 400 µM of commercially available casein phosphopeptide (CPP) was added to the second group, and no peptide was added to the third group The Fluo-3-AM containing Caco-2 cell suspension was excited at a wavelength of 488 nm, and the fluorescence intensity was recorded at a wavelength of 538 nm. The fluorescence intensity of each group of cells was as shown in FIG. 1. Furthermore, by the change in the fluo-3 fluorescence intensity in each group of Caco-2 cells, the percentage increases in the Caco-2 cells of the first group and the second group relative to the peak calcium ions (peak [Ca2+]) in the third group of Caco-2 cells are calculated. The results are shown in FIG. 2.

Figure 2:
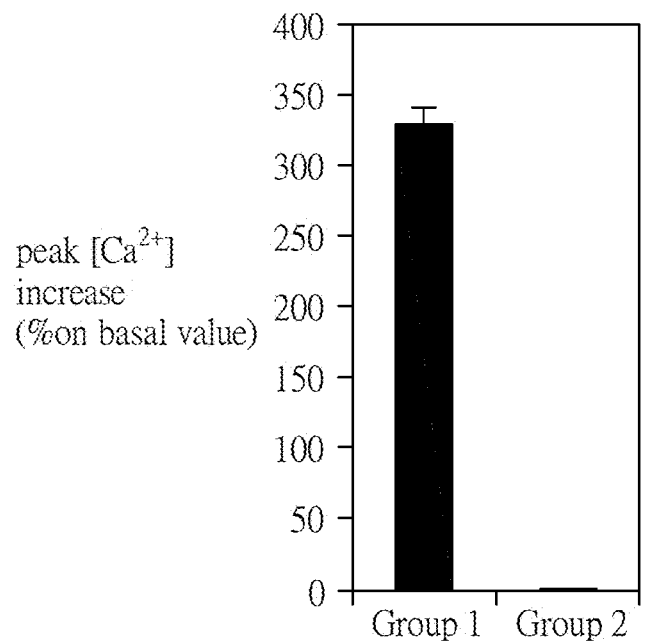
FIG. 2 shows the changes in fluorescence intensity of the first group and the second group relative to the first group calculated with the third group in FIG. 1 as a reference.

As can be known from the results shown in FIGS. 1 and 2, the fluorescence intensity in the first group of Caco-2 cells is significantly higher than that in the second group and the third group, and it is found through the comparison of the changes of the peak calcium ions in each group that the calcium ion concentration in the first group of Caco-2 cells is significantly increased compared to the second and third groups. As can be known, the peptide of SEQ ID No. 1 disclosed in the present invention does have the ability to transport calcium ions into cells.

Example 4: Cell Assay (II)

The Fluo-3-AM containing Caco-2 cell suspension was divided into six groups. At the 154th second, the following concentrations of calcium ions were added sequentially to each group: 0 mM, 0.3 mM, 0.5 mM, 1.5 mM, 3 mM, 6 mM, and at the 320th second, 400 µM of the peptide of SEQ ID No. 1 of the present invention was added respectively. The change in fluo-3 fluorescence intensity in each group of Caco-2 cells and the change in peak [Ca2+] concentration in each group were observed and analyzed following the methods as described in Example 3. The results are shown in FIGS. 3 and 4.

Figure 3:
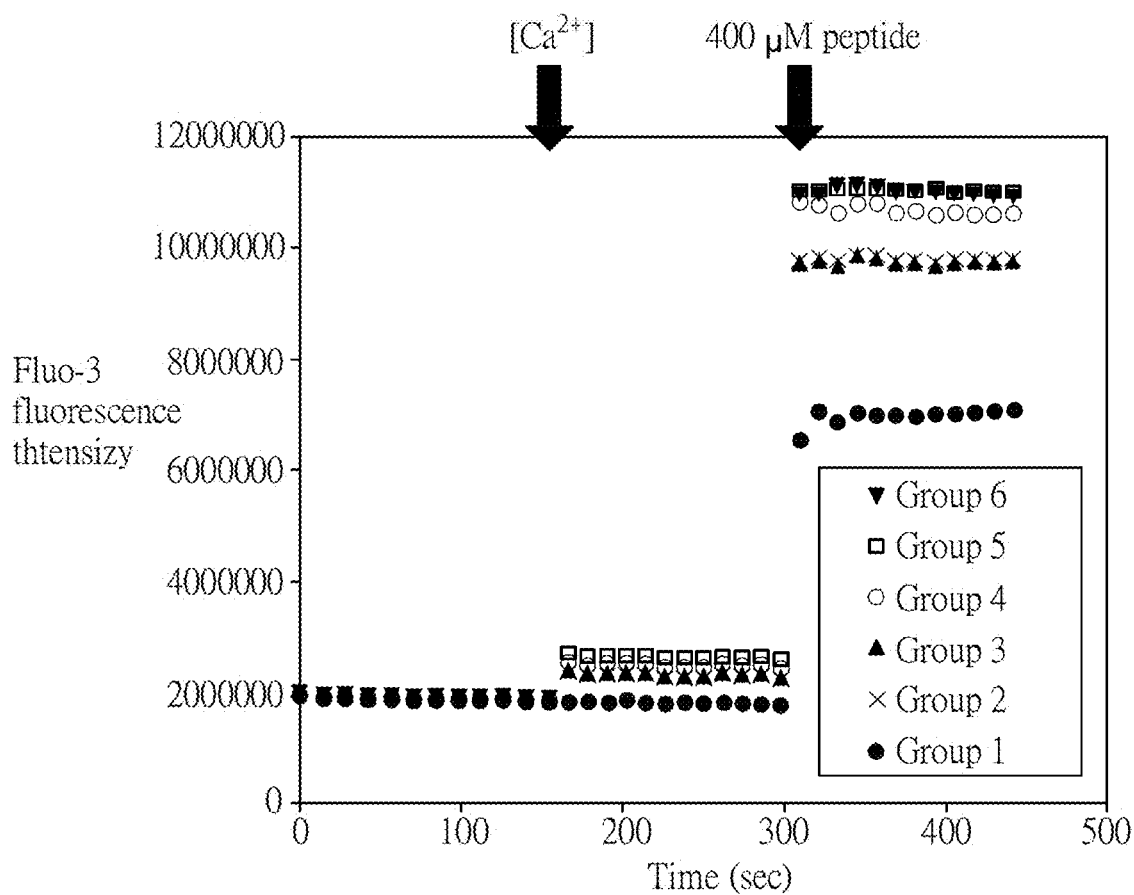
FIG. 3 shows the changes in fluorescence intensity of each group of Caco-2 cells treated with various concentrations of calcium ions.
Figure 4:
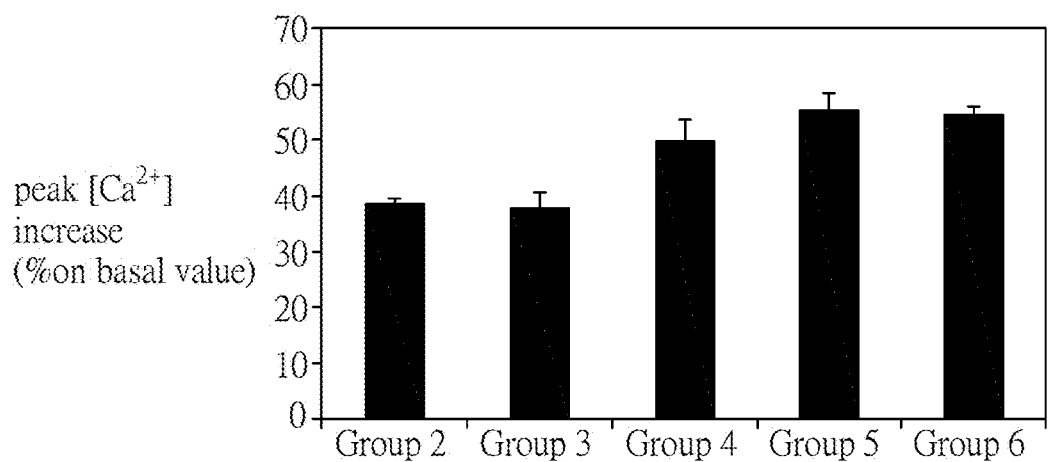
FIG. 4 shows the percentage increases in fluorescence intensity of the second to fifth groups relative to the first group calculated with the first group in FIG. 3 as a reference.

As can be seen from the results shown in FIGS. 3 and 4, at the 442th second, the fluorescence intensities in the first to sixth groups of Caco-2 cells are U.S. Pat. Nos. 7,059,148, 9,780,517, 9,720,348, 10,604,175, 10,986,171, and 10,912,015 respectively. Compared with the first group, the percentage increases of calcium ions in the second to sixth groups are 38.6%, 37.7%, 50.2%, 55.6%, and 54.6%, respectively.

The above results show that the peptide of SEQ ID No. 1 disclosed in the present invention is capable of transporting calcium ions into cells, and the concentration of calcium ions entering the cells increases as the concentration of calcium ions outside the cells increases. It can be seen that the peptide of SEQ ID No. 1 disclosed in the present invention can transport different doses of calcium ions into the cells.

Example 5: Cell Assay (III)

Figure 5:
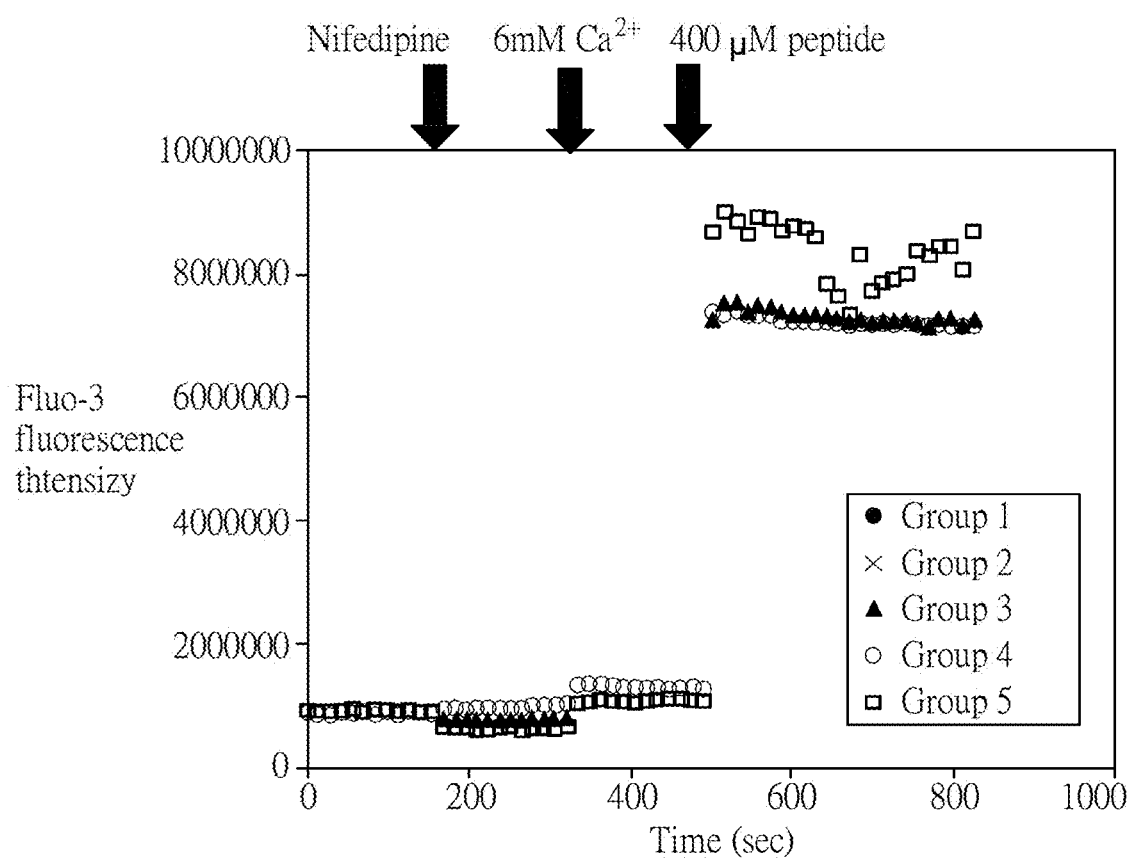
FIG. 5 shows the changes in fluorescence intensity of each group of Caco-2 cells treated with various concentrations of L-type potential sensitive calcium ion channel inhibitor.

The Fluo-3-AM containing Caco-2 cell suspension was divided into five groups. At the 154th second, the following concentrations of nifedipine were added sequentially to each group respectively: 0 µM, 10 µM, 20 µM, 50 µM, and 100 µM, at the 320th second, 6 mM of calcium ions was respectively added to each group, and at the 502th second, 400 µM of the peptide of SEQ ID No. 1 of the present invention was added to each group respectively. The changes in fluo-3 fluorescence intensity in each group of Caco-2 cells were observed and analyzed under the conditions as described in Example 3. The results are shown in FIG. 5.

Since the drug nifedipine is an inhibitor for L-type potential-sensitive calcium channel, the administration of nifedipine prevents calcium ions from entering the cells via the L-type potential-sensitive calcium channel, leading to decreased fluorescence intensity in Caco-2 cells. However, the result in FIG. 5 shows that after the peptide of SEQ ID No. 1 of the present invention is administered, the fluorescence intensity in each of the groups is increased and no significant difference exists therebetween. In other words, the L-type potential-sensitive calcium channel inhibitor cannot block the entry of calcium ions into Caco-2 cells, and the peptide of SEQ ID No. 1 disclosed in the present invention can still transport calcium ions outside the cells into the cells.

As can be known, the peptide of SEQ ID No. 1 disclosed in the present invention transports calcium ions into cells via other pathways than the L-type potential-sensitive calcium channel.

Example 6: Cell Assay (IV)

The steps were the same as those described in Example 5, except that the calcium ion channel V6 inhibitor: ruthenium red (RUR) was administered at the 154th second. The changes in fluorescence intensity in each group of the Caco-2 cells are shown in FIG. 6.

Figure 6:
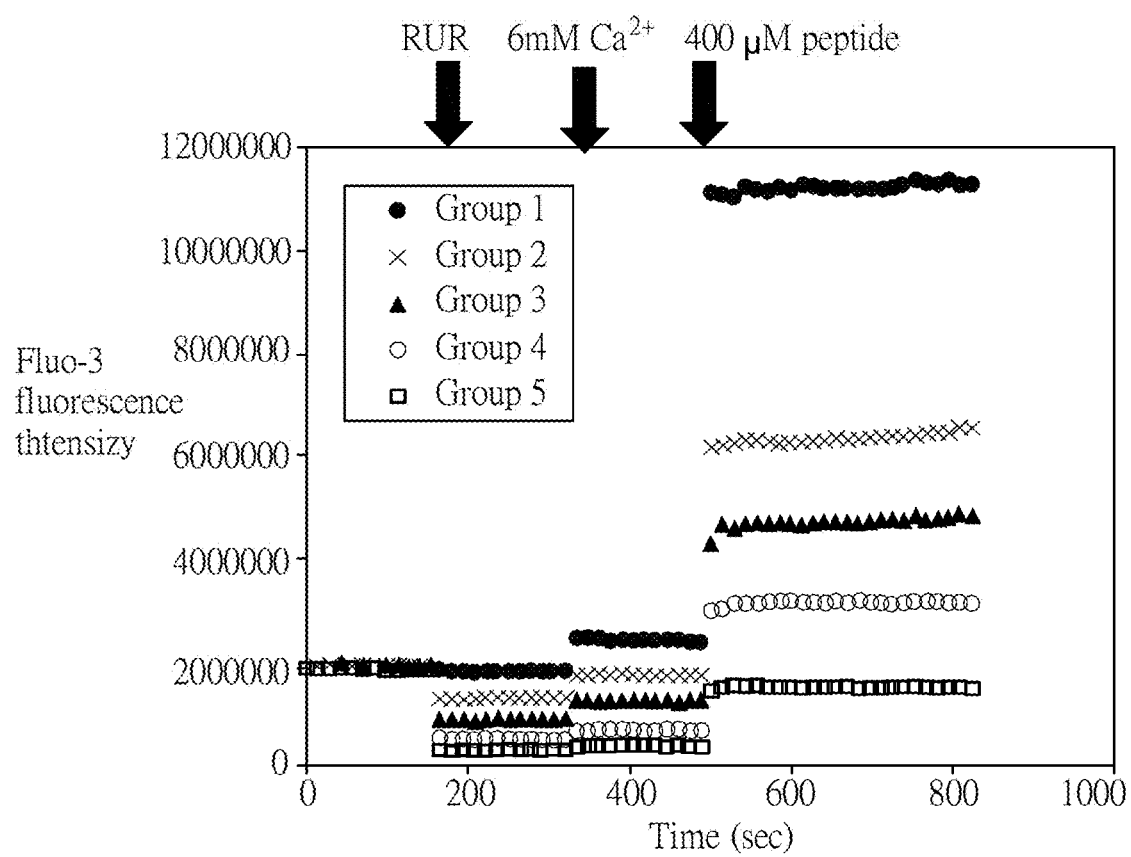
FIG. 6 shows the changes in fluorescence intensity of each group of Caco-2 cells treated with various concentrations of calcium ion channel V6 inhibitor.

As can be known from the results shown in FIG. 6, it is known that as the dose of ruthenium red administered increases, the fluorescence intensity in each of the Caco-2 cells declines. As further calculated from the results shown in FIG. 6, the percentage decreases of peak calcium ion (peak [Ca2+]) of the second to fifth groups, are 41.9%, 57.3%, 72.0%, and 86.7%, respectively compared to the first group. In other words, although the peptide having an amino acid sequence of SEQ ID No. 1 can transport the external calcium ions into the cells, when ruthenium red is administered to the cells, the calcium ions are prevented from entering the cells, and the concentration of calcium ions entering the cells will decrease as the dosage of ruthenium red administered increases.

Example 7: Establishment of Animal Model of Osteoporosis

The 8-week old male ICR mice were used to establish animal models of osteoporosis that were Akr1A1 gene deficient mice. The green fluorescent protein (eGFP) gene was introduced into the Akr1A1 locus on the fourth chromosome of the ICR male mice by gene mapping and implantation, and a 30-kb gene fragment in the exon 1-5 region of the Akr1A1 gene was knock out to disable the Akr1A1 gene, so as to prepare the model mice of osteoporosis.

Example 8: Animal Test

Akr1A1 gene-deficient male mice were divided into three groups and treated for 12 weeks according to the following conditions. The first group was given 400 mg/L vitamin C; the second group was untreated group, and given only water; and the third group was administered with the novel peptide disclosed in the present invention at a dose of 1.5 mg/kg/day.

After the experiment, the blood and the left and right femurs were taken from each group of mice. The blood was centrifuged to obtain red blood cell-free serum for subsequent analysis; the muscles were removed from the left and right femurs to which they are attached; then one femur was fixed with formalin and scanned with μ-CT; and the other femur was sterilized with 70% alcohol, then bone marrow was flushed out, and the cells were cultured for analysis in subsequent examples.

Example 9: Analysis of Reactive Oxygen Species/Reactive Nitrogen Species (ROS/RNS)

The serum and bone marrow effluent obtained from each group of mice in Example 9 at 20 weeks of age were used as samples to be analyzed in this example.

The samples to be analyzed were analyzed using a reactive oxygen species/reactive nitrogen species detection kit (OxiSelect™ In Vitro ROS/RNS Assay Kit, Green Fluorescence). The process was as follows. A standard solution (DCF), a catalyst and a DCFH solution (2.7-Dichlorofluorescndacetate) were prepared. 50 μL of the sample to be analyzed was added to a black 96-well plate, and then 50 μL of the catalyst was added and reacted for 5 minutes. 100 μL of the DCFH solution was added, and reacted at room temperature for 30 minutes in the dark. After the reaction was completed, the fluorescent DCF in the sample to be analyzed was detected by a multi-functional plate reader with 480-nm excitation/530-nm emission. The serological test results are shown in FIG. 7A, and the detection results of the bone marrow effluent are shown in FIG. 7B.

Figure 7A:
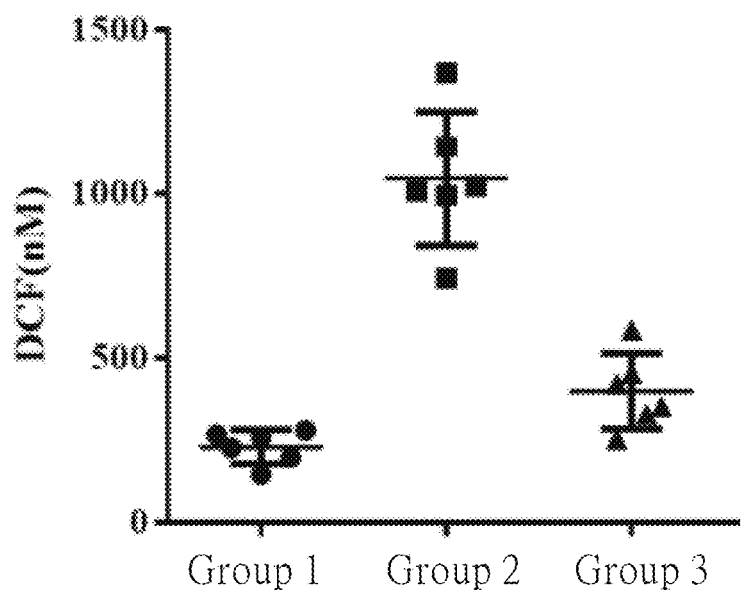
FIG. 7A shows the content of reactive oxygen species/reactive nitrogen species assayed in the serum of each group of mice at 20 weeks of age.
Figure 7B:
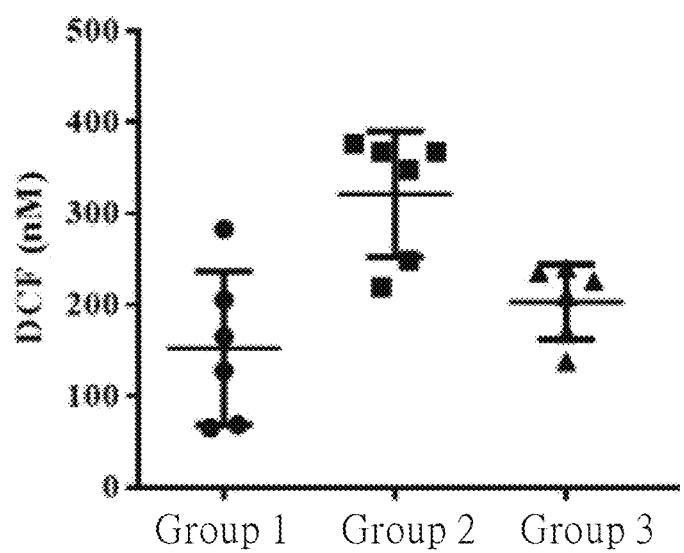
FIG. 7B shows the content of reactive oxygen species/reactive nitrogen species assayed in the femur of each group of mice at 20 weeks of age.

From the results shown in FIGS. 7A and 7B, it can be seen that compared with the first group of mice, the second group of mice not administered with vitamin C have significantly increased oxidative stress in the body and the bone; and the third group of mice administered with the peptide of the present invention have a content of reactive oxygen species in the body and the bone that is obviously reduced compared with the second group, and is close to those of the first group of mice, showing that the peptide of SEQ ID No. 1 disclosed in the present invention can inhibit the concentration of free radicals in the body and in the bone, and the effect becomes increasingly better with the increasing duration of administration.

Previous studies have pointed out that too high concentrations of reactive oxygen species/reactive nitrogen species will inhibit the production of osteoblasts, and promote the apoptosis of bone cells and the differentiation of osteoclasts. Therefore, reactive oxygen species/reactive nitrogen species are considered to be a factor causing osteoporosis. The in-vivo concentration of free radicals can be effectively reduced by administering the peptide of SEQ ID No. 1 of the present invention, thereby promoting the production of bone cells and inhibiting the differentiation of osteoclasts, to achieve the efficacy of treating or preventing osteoporosis-related conditions. In addition, increased oxidative stress in the body impairs the cells and enhances the performance of pro-inflammatory factors, leading to the occurrence of inflammation-related diseases. Therefore, the increased oxidative stress in the body can be reduced by administration of the peptide of SEQ ID No. 1 disclosed in the present invention, to achieve the effect of preventing or/and treating inflammation-related diseases.

Example 10: Thiobarbituric Acid Reactive Substance (TBARS) Assay

Figure 8:
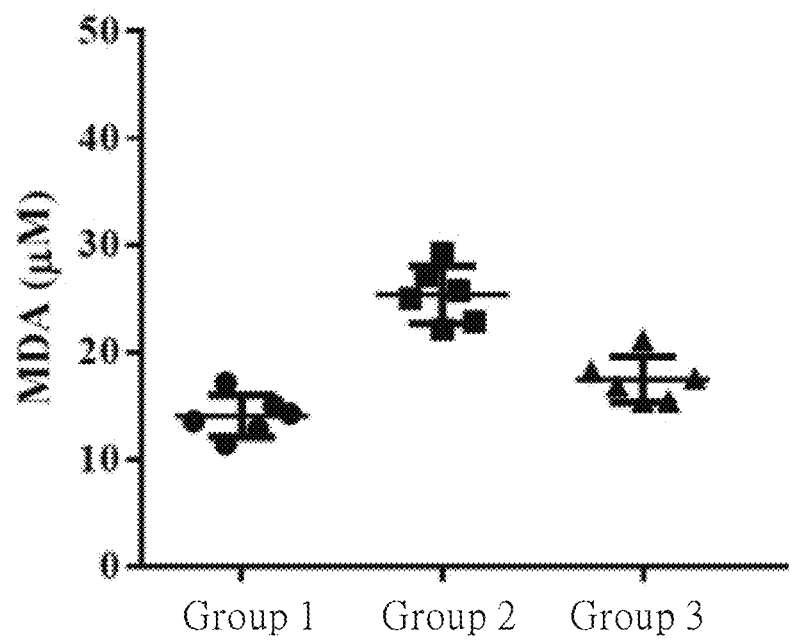
FIG. 8 shows the malondialdehyde level assayed in the serum of each group of mice at 20 weeks of age.

The serum obtained from each group of mice at 20 weeks of age in Example 8 was analyzed using a Thiobarbituric acid reactive substance assay kit (Cayman, Ann Arbor, Mich., USA). The process was as follows. Standard solutions and a staining reagent were prepared. For each concentration of standard solution and serum, 100 μL of TBA SDS solution was added to a 15 ml test tube, then 100 μL of various concentrations of standard solutions and serum were added, and finally 4 mL of the staining agent was added. The tube was heated in a water bath at 100° C. for 1 hour, and immediately cooled for 10 minutes after heating to terminate the reaction. After cooling, the test tube was centrifuged for 10 minutes at 1600×g at 4° C., and then stood at room temperature (25° C.). 150 μL of the supernatant was taken, the concentration of sample to be analyzed was determined using an enzyme immunoassay microplate reader (Multiskan EX) at a wavelength of 535 nm, and the serum malondialdehyde (MDA) content was calculated from a standard curve. The serological analysis results of each group of mice are shown in FIG. 8.

According to previous studies, an increase in in-vivo malondialdehyde content indicates an increase in oxidative stress in the body, which not only increases the pro-inflammatory factors, but also activates osteoclasts, leading to osteoporosis or a high risk of osteoporosis-related conditions. From the results shown in FIG. 8, the content of malondialdehyde in the serum of the second group of mice is significantly higher than that in the first group of mice, indicating abnormal lipid peroxidation and metabolism of the second group of mice, resulting in an imbalance in bone metabolism. By administering the peptide of the present invention, the malondialdehyde content in the serum of the third group of mice is significantly lower than that in the second group of mice, and is similar to that in the first group of mice, showing that the serum malondialdehyde content can be effectively reduced by administering the peptide of SEQ ID No. 1 of the present invention, thus achieving the effects of preventing or treating osteoporosis-related diseases and inflammation-related diseases.

Example 11: Superoxide Dismutase Assay

Figure 9:
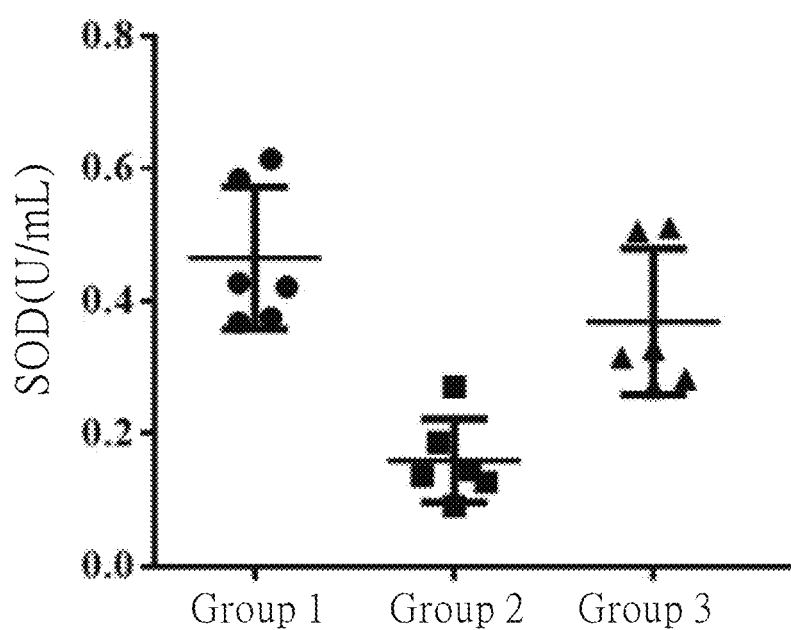
FIG. 9 shows the superoxide dismutase level assayed in the serum of each group of mice at 20 weeks of age.

The serum obtained from each group of mice at 20 weeks of age in Example 8 was analyzed using a superoxide dismutase assay kit (Cayman, Ann Arbor, Mich., USA). Standard solutions, a radical detector and xanthine oxidase were prepared. Then 200 μL of the radical detector, 10 μL of each concentration of the standard solution and serum were sequentially added to a 96-well plate. Finally, 20 μL of xanthine oxidase was added, and reacted for 30 minutes with shaking at room temperature. The serum concentration was determined using an enzyme immunoassay microplate reader (Multiskan EX) at a wavelength of 454 nm. The content of superoxide dismutase in the serum was calculated from a standard curve. The serological test results of each group of mice are shown in FIG. 9.

Example 12: Catalase Assay

The serum obtained from each group of mice at 20 weeks of age in Example 8 was analyzed using a catalase assay kit (Cayman, Ann Arbor, Mich., USA). The process was as follows. Standard solutions, a catalase assay buffer, a catalase sample buffer, and Catalase Hydrogen Peroxide were prepared. 100 μL of the catalase assay buffer, 30 μL of methanol, and 20 μL of each concentration of standard solution and serum were sequentially added to a 96-well plate and mixed uniformly. Then, 20 μL of catalase was added and reacted for 20 minutes at room temperature with shaking. After the reaction, 30 μL of potassium hydroxide and 30 μL of Catalase Purpald (Chromogen) were added, and reacted for 10 minutes at room temperature with shaking. Finally, 10 μL of Catalase Potassium Periodate was added, and reacted for 5 minutes at room temperature with shaking. The serum concentration was determined using an enzyme immunoassay microplate reader at a wavelength of 540 nm. The serum concentration was calculated from a standard curve, to obtain the catalase content in the serum. The test results are shown in FIG. 10.

Previous studies pointed out that superoxide dismutase and catalase are important antioxidants in the body. If their content is too low, they will not be able to scavenge free radicals in the body, causing the cells to withstand high oxidative stress and thus increased occurrence of inflammatory reactions in the organs of the body, as well as suppressed proliferation of osteoblasts and differentiation of chondrocytes. Therefore, the osteogenesis is affected, causing the exacerbation of osteoporosis-related disorders or a high risk of osteoporosis.

Figure 10:
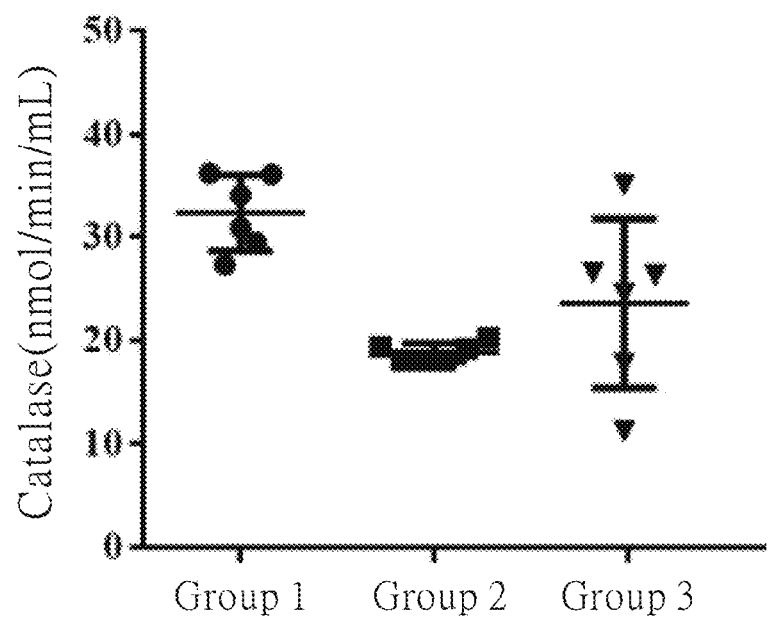
FIG. 10 shows the hydrogen peroxidase level assayed in the serum of each group of mice at 20 weeks of age.

Referring to FIGS. 9 and 10, as can be known from the results of Examples 11 and 12, the antioxidant enzyme content in the serum of the second group of mice is significantly lower than that in the first group of mice, showing that the second group of mice suffer from high oxidative stress and are unable to scavenge free radicals in the body. The third group of mice administered with the peptide of the present invention have a serum antioxidant enzyme content that is higher than that in the second group of mice, and is close to that in the first group of mice, showing that the peptide of the present invention can enhance the in-vivo activity of antioxidant enzymes, thus achieving the effects of scavenging free radicals and reducing oxidative stress in the body.

Therefore, as shown by the results in FIGS. 9 and 10, the concentrations of superoxide dismutase and catalase in serum can be lowered by administering the peptide of SEQ ID No. 1 of the present invention, so as to avoid the inhibition of oxidative stress on osteogenesis, thus effectively achieving the efficacy of treating or preventing osteoporosis-related disorders and inflammatory diseases.

Example 13: Proinflammatory Factor Assay

The serum obtained from each group of mice at 20 weeks of age in Example 8 was analyzed respectively using the IL-1 Mouse SimpleStep ELISA kit (abcam, Cambridge, Mass., USA), the IL-6 Mouse ELISA kit (abcam, Cambridge, Mass., USA), and the TNF-α Mouse SimpleStep ELISA kit (abcam, Cambridge, Mass., USA).

The process for detecting the concentration of IL-1 or TNF-α in serum was as follows. 50 μL/well of the prepared standard solution and serum and 50 μL/well of an antibody cocktail were added to a 96-well plate, incubated at room temperature for one hour, and then washed. 100 μL/well of a TMB substrate solution was added and reacted for about 10 minutes at room temperature in the dark. Finally, 100 μL/well of a stop solution was added. The serum concentration was determined using an enzyme immunoassay microplate reader at a wavelength set to 450 nm. The IL-1β or TNF-α concentration in the serum was obtained after calculation.

The process for detecting the concentration of IL-6 in serum was as follows. 100 μL/well of the prepared standard solution and serum (2×) were added to a 96-well plate, incubated at room temperature for 2.5 hours, and then washed. 100 μL/well of 1× biotinylated IL-6 detection antibody was added, incubated at room temperature for 1 hours, and then washed. 100 μL/well of HRP streptavidin solution was added, incubated at room temperature for 45 minutes, and then washed. 100 μL/well of TMB one-step substrate reagent was added, and reacted for about 30 minutes at room temperature in the dark. Finally, 50 μL/well of a stop solution was added. The serum concentration was determined using an enzyme immunoassay microplate reader at a wavelength set to 450 nm. The IL-6 concentration in the serum was obtained after calculation.

Figure 11:
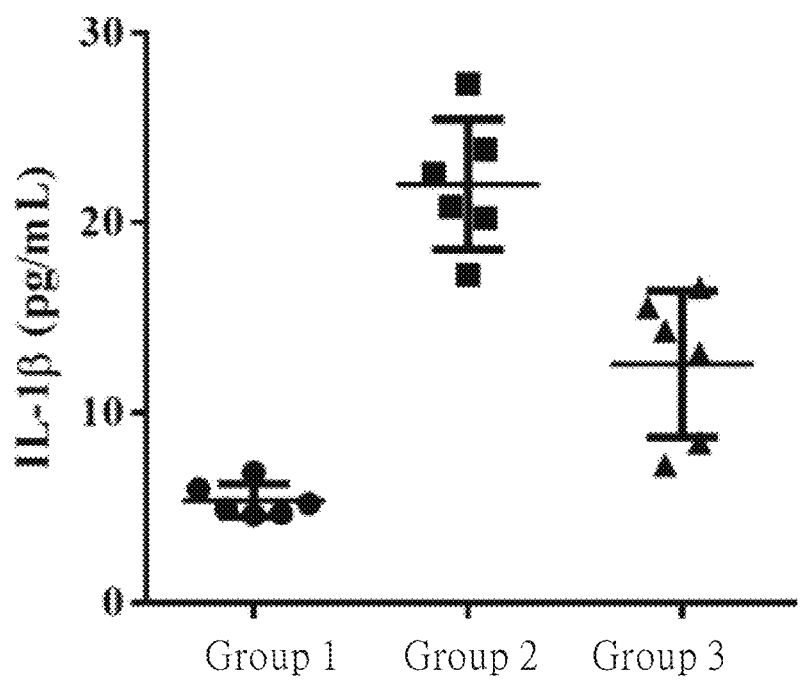
FIG. 11 shows the IL-1β level assayed in the serum of each group of mice at 20 weeks of age.
Figure 12:
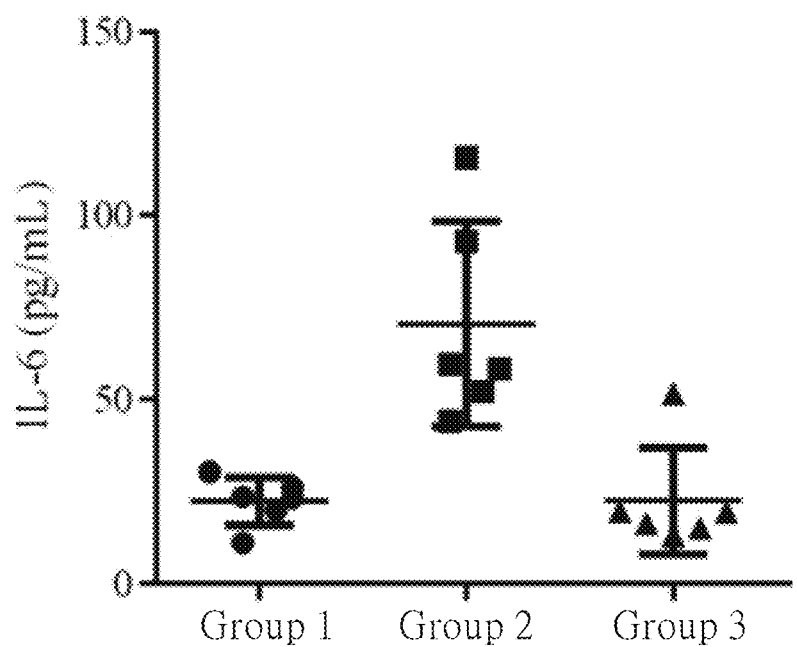
FIG. 12 shows the IL-6 level assayed in the serum of each group of mice at 20 weeks of age.
Figure 13:
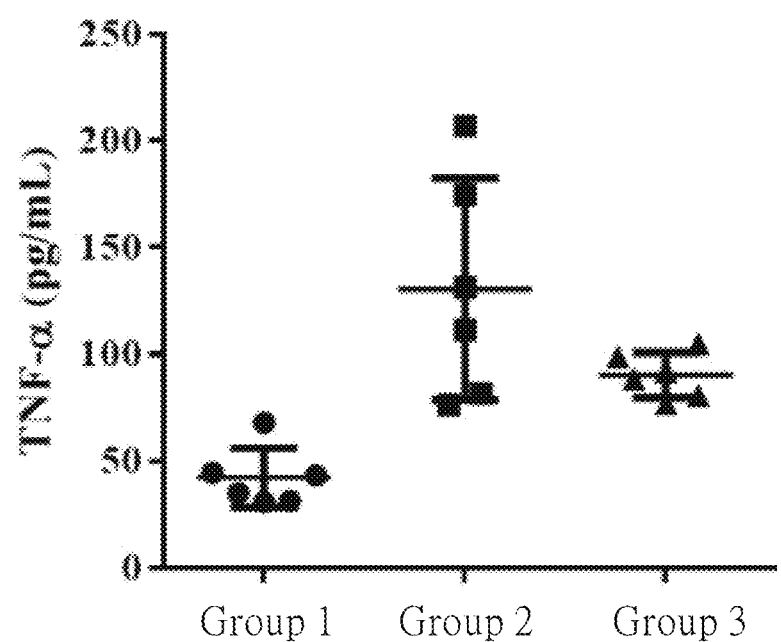
FIG. 13 shows the TNF-α level assayed in the serum of each group of mice at 20 weeks of age.

The IL-1β, IL-6 and TNF-α levels assayed in the serum of each group of mice are shown in FIG. 11 to FIG. 13 respectively.

Previous literatures pointed out that when the cytokines associated with inflammation, such as IL-1β, IL-6, and TNF-α, increase, not only chronic inflammation-related diseases are caused, but also the proliferation of osteoclasts is stimulated, leading to accelerated bone loss, exacerbated osteoporosis-related conditions or increased risk of osteoporosis.

As can be known from the results of FIGS. 11 to 13, the pro-inflammatory factor in the second group of mice is significantly higher than that in the first group of mice, and the third group of mice administered with the peptide of the present invention have an in-vivo content of pro-inflammatory factor that is significantly lower than that in the second group of mice, and is close to the serum content in the first group. The above results show that administration of the peptide of SEQ ID No. of the present invention can reduce the in-vivo concentration of inflammation-related cytokines, and thus reduce the chance of occurrence of inflammatory diseases and inhibit the proliferation of osteoclasts, thereby avoiding the rapid loss of bone and achieving the efficacy of preventing and/or treating osteoporosis-related diseases.

Example 14: Determination of Bone Metabolism Indices

The serum or femoral bone marrow effluent obtained from each group of mice at 20 weeks of age in Example 8 was used as a sample to be analyzed in this example, and analyzed using the P1NP (Procollagen☐N-Terminal Propeptide) assay kit (Uscn Life Science Inc., Wuhan, China), CTX-1 (Cross Linked C-Telopeptide Of Type I Collagen) ELISA kit (Uscn Life Science Inc., Wuhan, China), Osteocalcin ELISA kit (Uscn Life Science Inc., Wuhan, China), mouse osteoprotegerin (OPG)/TNFRSF11B immunoassay kit (R&D System Inc., MN, USA), and mouse TRANCE/RANKL/TNFSF11 immunoassay kit (R&D System Inc., MN, USA).

Figure 14A:
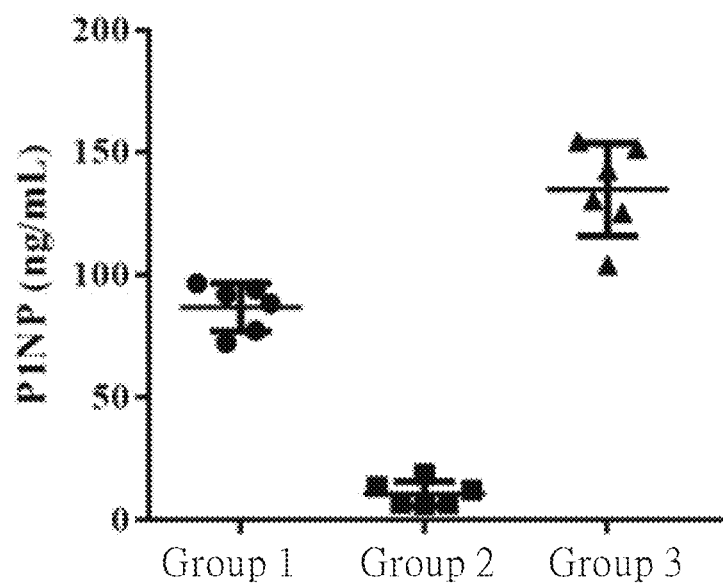
FIG. 14A shows the P1NP level assayed in the serum of each group of mice at 20 weeks of age.
Figure 14B:
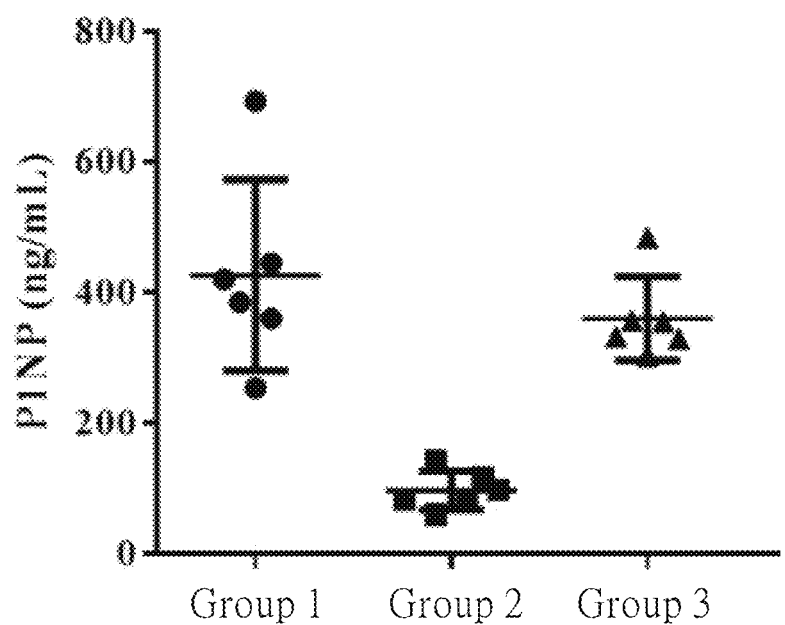
FIG. 14B shows the P1NP level assayed in the femur of each group of mice at 20 weeks of age.

The process for detecting the concentration of P1NP in the sample to be analyzed was as follows. The standard solution and the sample (100 times) were diluted and prepared, and then 100 μL/well of the standard solution and the sample were added to a 96-well plate and incubated at 37° C. for 1 hour. The liquid in the plate was removed, and 100 μL/well of a detection reagent A was added, incubated for one hour, and then washed. 100 μL/well of a detection reagent B was added, incubated for 30 minutes, and then washed. 90 μL/well of a substrate solution was added and reacted for 15 minutes. Finally, 50 μL/well of a stop solution was added. The concentration of the sample to be analyzed was determined using an enzyme immunoassay microplate reader at a wavelength set to 450 nm. The P1NP concentration in the sample to be analyzed was obtained after calculation. The P1NP content detected in the serum of each group of mice is shown in FIG. 14A. The P1NP content detected in the femur of each group of mice is shown in FIG. 14B.

Figure 15A:
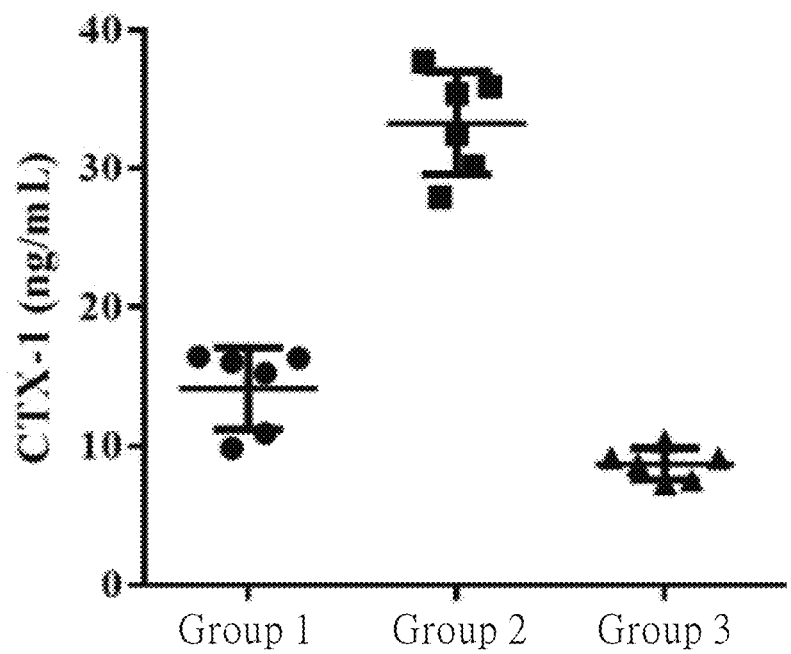
FIG. 15A shows the CTX-1 level assayed in the serum of each group of mice at 20 weeks of age.
Figure 15B:
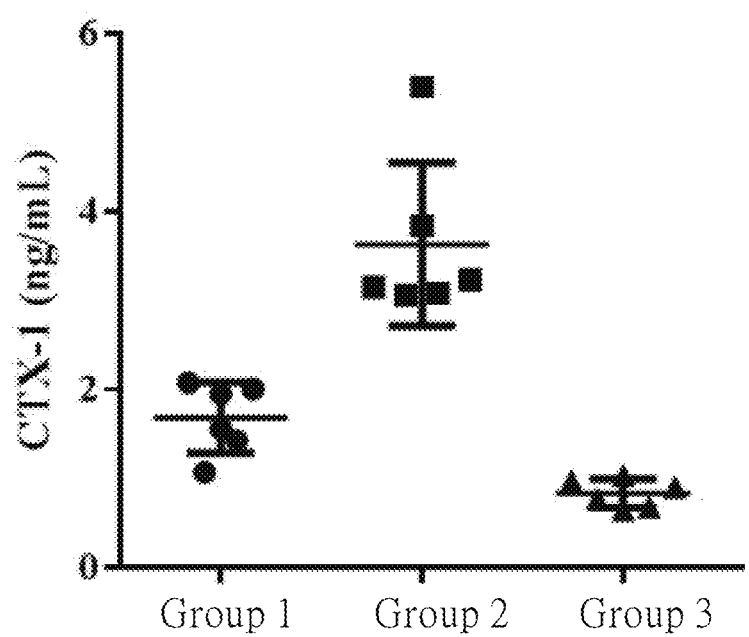
FIG. 15B shows the CTX-1 level assayed in the femur of each group of mice at 20 weeks of age.
Figure 16A:
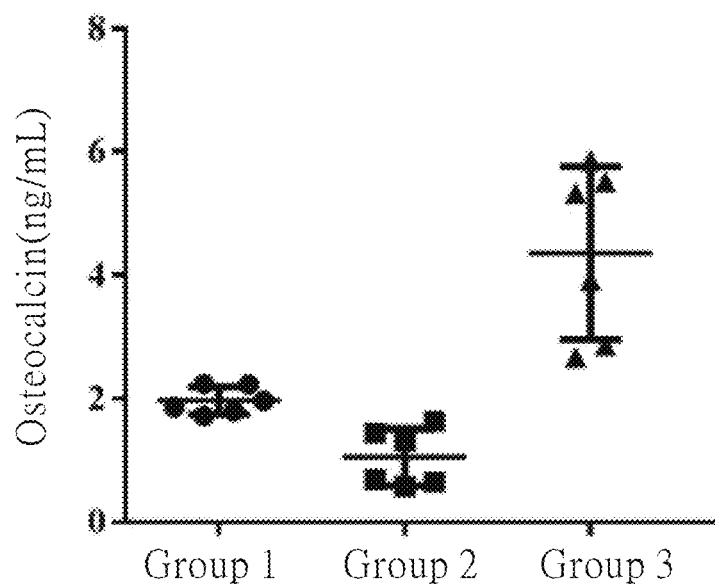
FIG. 16A shows the osteocalcin assayed in the serum of each group of mice at 20 weeks of age.
Figure 16B:
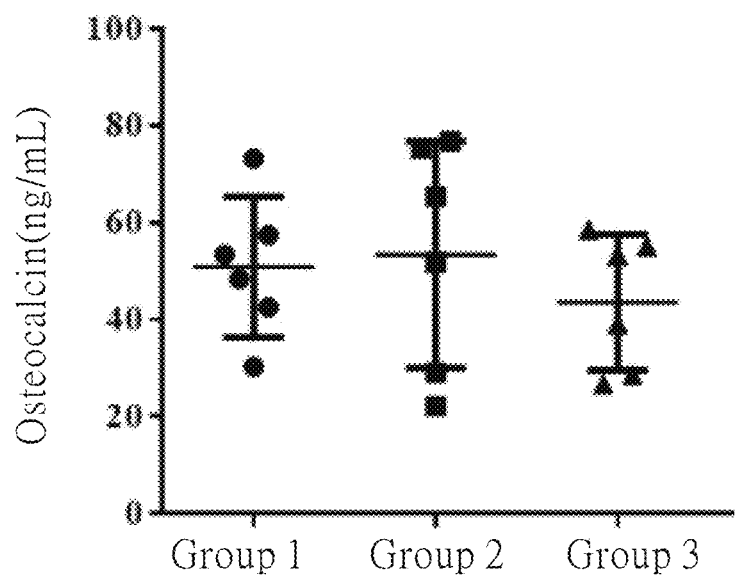
FIG. 16B shows the osteocalcin assayed in the femur of each group of mice at 20 weeks of age.

The process for detecting the concentration of CTX-1 or osteocalcin in the sample to be analyzed was as follows. The standard solution and the sample to be analyzed (10 times) were diluted and prepared. 50 μL/well and 50 μL/well of a detection reagent A were added to a 96-well plate, incubated for 1 hour at 37° C., and then washed. 100 μL/well of a detection reagent B was added, incubated for 30 minutes, and then washed. 90 μL/well of a substrate solution was added and reacted for 15 minutes. Finally, 50 μL/well of a stop solution was added. The concentration of the sample to be analyzed was determined using an enzyme immunoassay microplate reader at a wavelength set to 450 nm. The CTX-1 or osteocalcin concentration in the sample to be analyzed was obtained after calculation. The CTX-1 content detected in the serum of each group of mice is shown in FIG. 15A. The CTX-1 content detected in the femur of each group of mice is shown in FIG. 15B. The osteocalcin content detected in the serum of each group of mice is shown in FIG. 16A. The osteocalcin content detected in the femur of each group of mice is shown in FIG. 16B.

Figure 17:
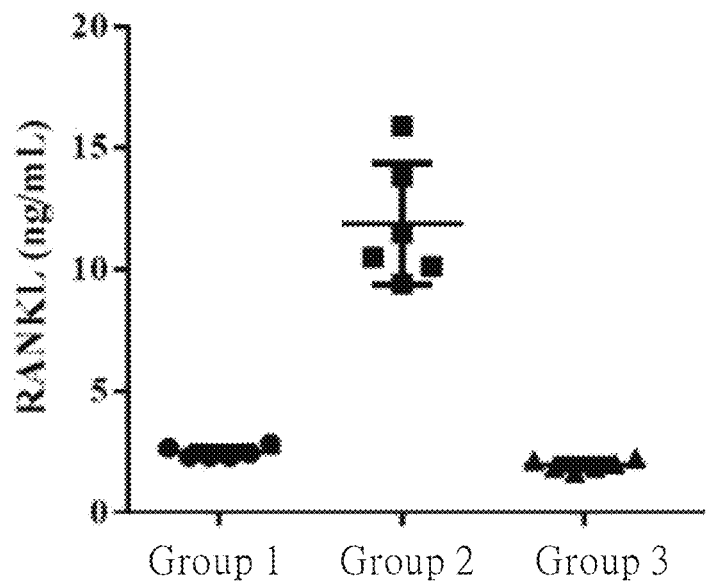
FIG. 17 shows the RANKL level assayed in the serum of each group of mice at 20 weeks of age.

The process for detecting the concentration of receptor activator of nuclear factor kappa-B ligand (RANKL) in serum was as follows. 50 μL/well of the assay diluent RD1W was added to a plate coated with specific monoclonal anti-rat TRANCE antibody. 50 μL/well of a standard solution and serum were added, incubated at room temperature for 2 hours, and then washed. 100 μL/well of mouse TRANCE/RANKL conjugate was added, incubated at room temperature for 2 hours, and then washed. 100 μL/well of a substrate solution was added, and incubated at room temperature for 30 minutes in the dark. Finally, 100 μL/well of a stop solution was added. The serum concentration was determined using an enzyme immunoassay microplate reader at a wavelength set to 450 nm. The serum RANKL concentration was obtained after calculation. The RANKL concentration detected in the serum of each group of mice is shown in FIG. 17.

Figure 18:
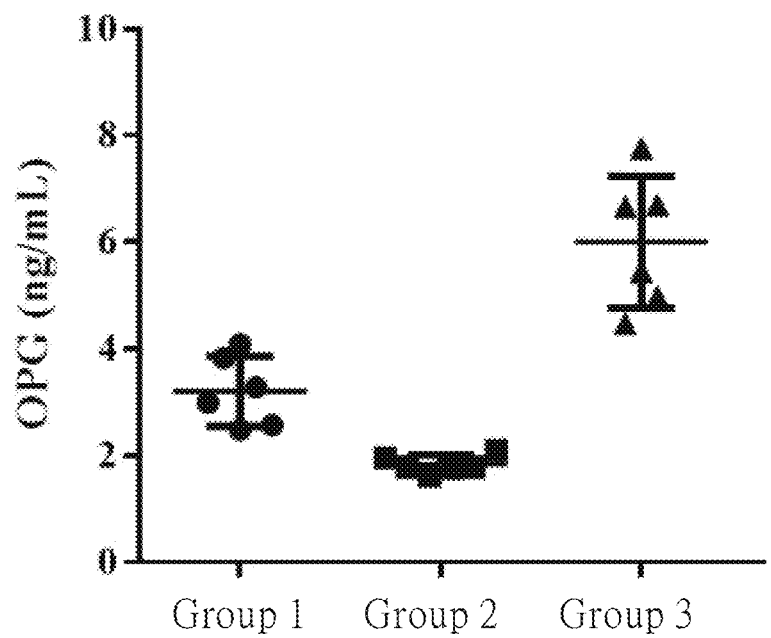
FIG. 18 shows the osteoprotegerin level assayed in the serum of each group of mice at 20 weeks of age.

The process for detecting the concentration of osteoprotegerin in the serum was as follows. 50 μL/well of the assay diluent RD1-21 was added to a plate coated with specific monoclonal anti-rat osteoprotegerin antibody. 50 μL/well of a standard solution and serum were added, incubated at room temperature for 2 hours, and then washed. 100 μL/well of mouse osteoprotegerin conjugate was added, incubated at room temperature for 2 hours, and then washed. 100 μL/well of a substrate solution was added, and incubated at room temperature for 30 minutes in the dark. Finally, 100 μL/well of a stop solution was added. The serum concentration was determined using an enzyme immunoassay microplate reader at a wavelength set to 450 nm. The serum osteoprotegerin concentration was obtained after calculation. The osteoprotegerin concentration detected in the serum of each group of mice is shown in FIG. 18.

Figure 19:
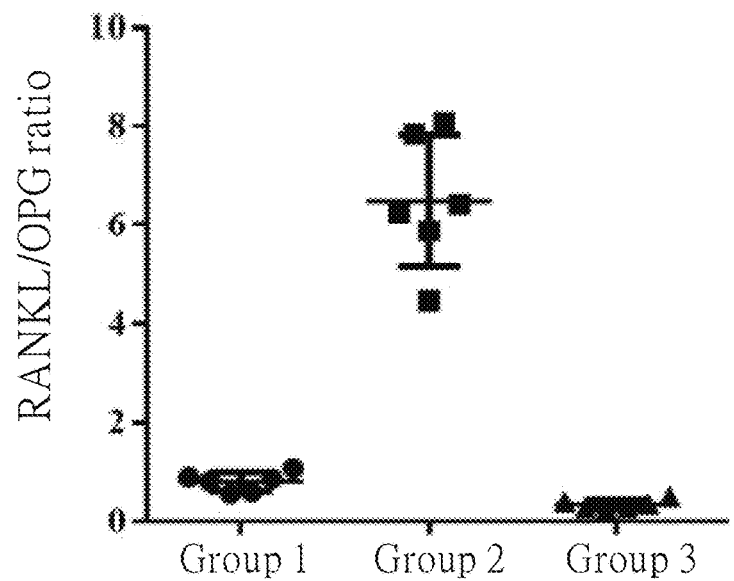
FIG. 19 shows the ratio of RANKL to osteoprotegerin in the serum of each group of mice.
Figure 20:
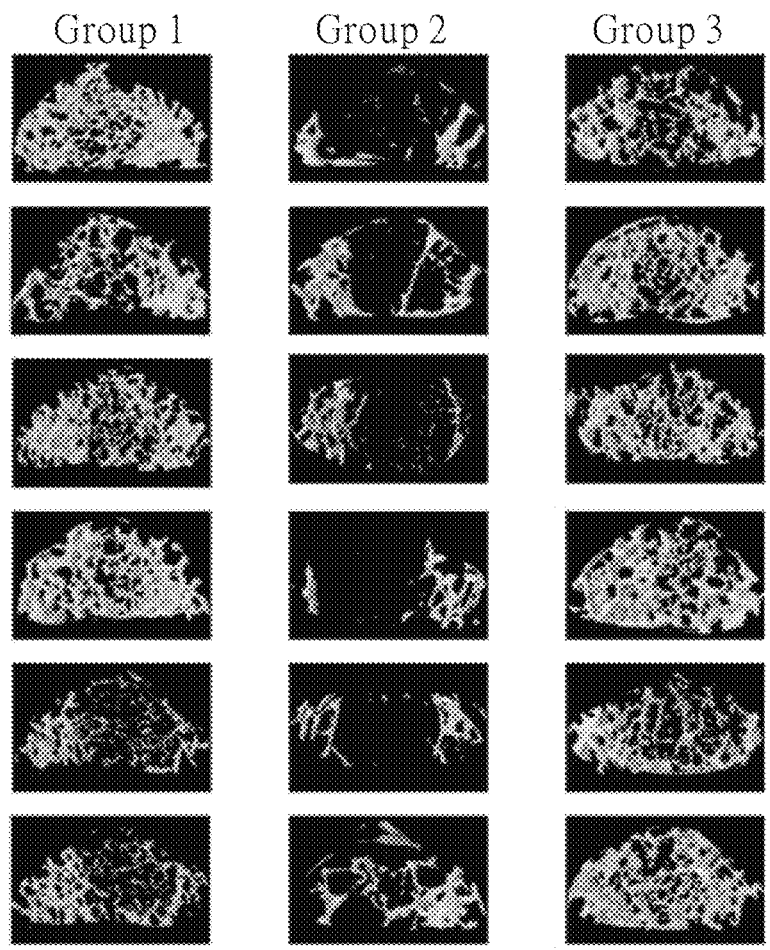
FIG. 20 shows the changes in trabecular structure of each group of mice.
Figure 21:
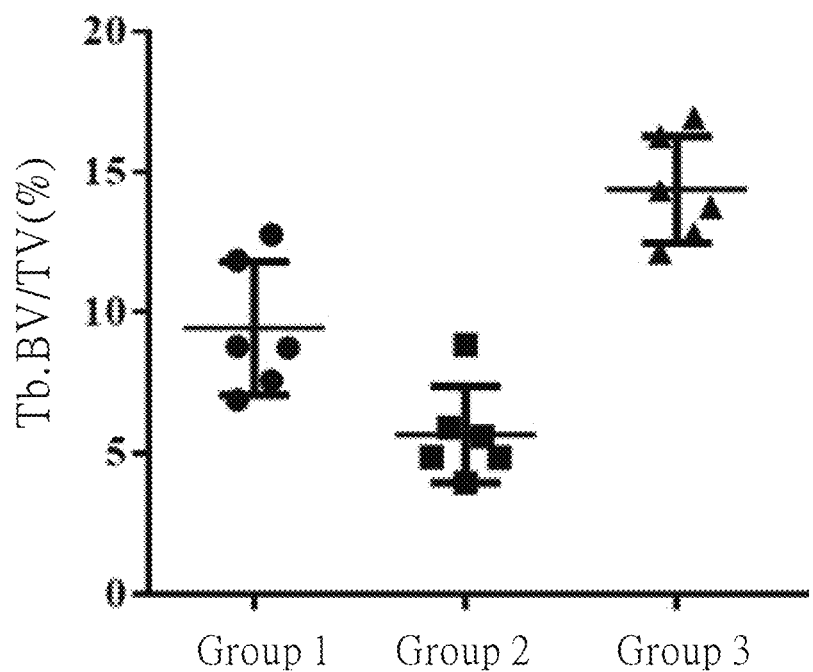
FIG. 21 shows the trabecular bone volume-total volume ratio of each group of mice.
Figure 22:
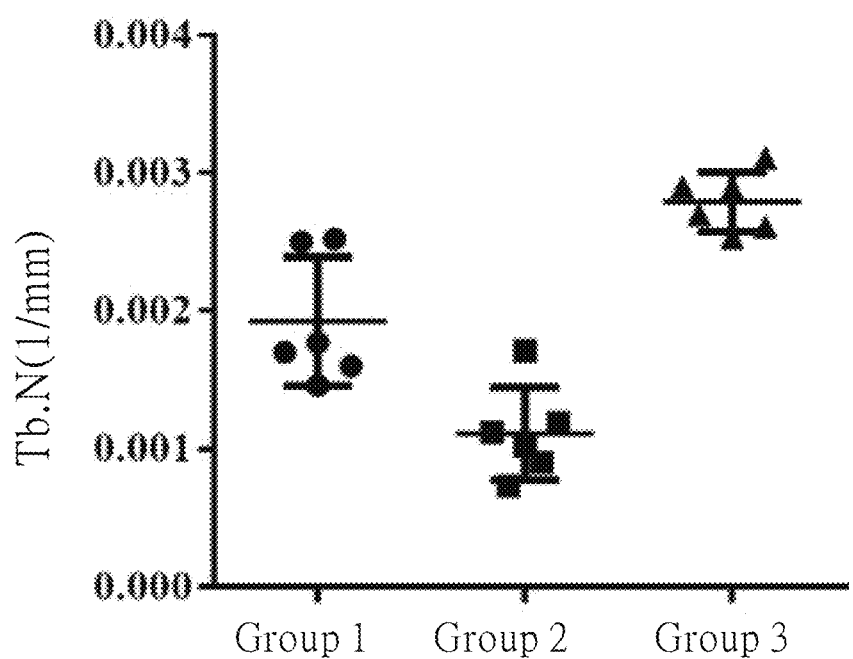
FIG. 22 shows the trabecular number of each group of mice.
Figure 23:
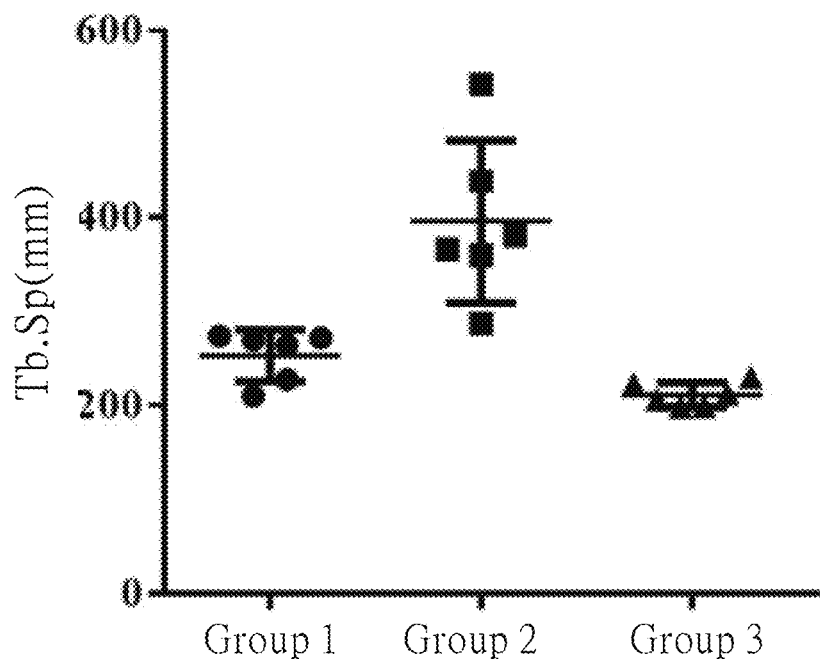
FIG. 23 shows the trabecular spacing of each group of mice.
Figure 24:
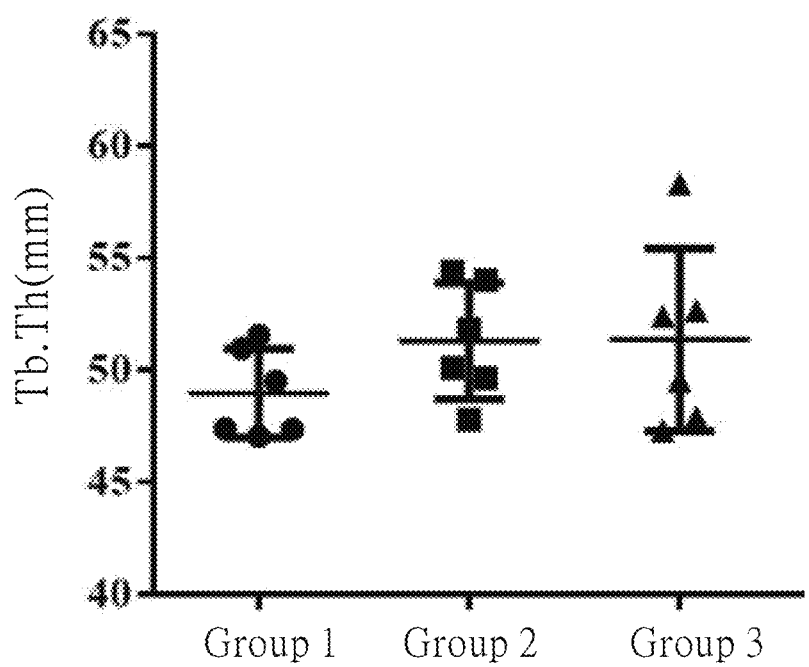
FIG. 24 shows the average trabecular thickness of each group of mice.
Figure 25:
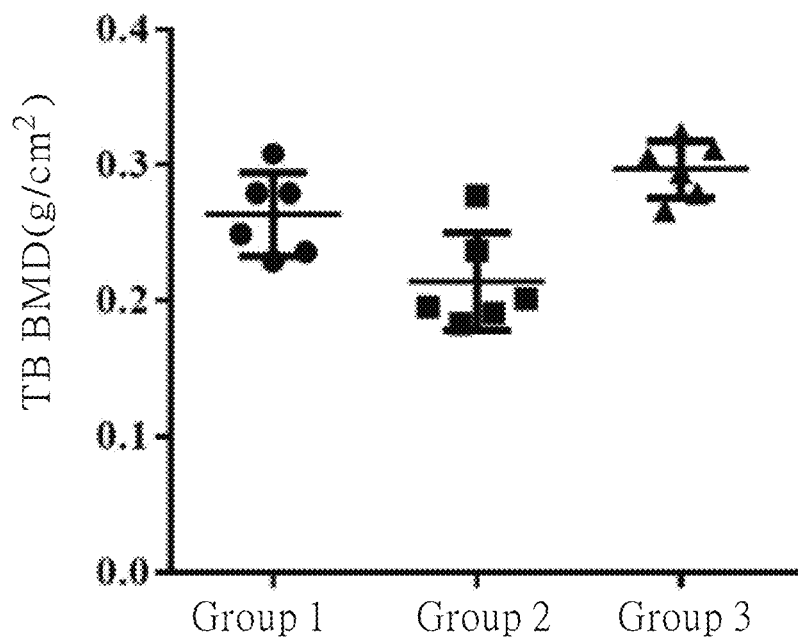
FIG. 25 shows the trabecular bone mineral density of each group of mice.
Figure 26:
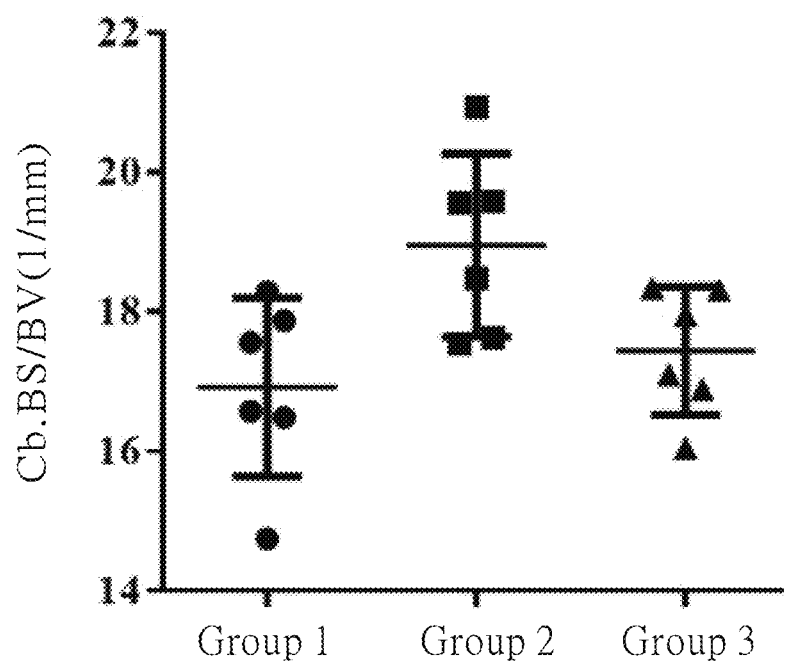
FIG. 26 shows the cortical bone surface-area-to-bone-volume ratio of each group of mice.
Figure 27:
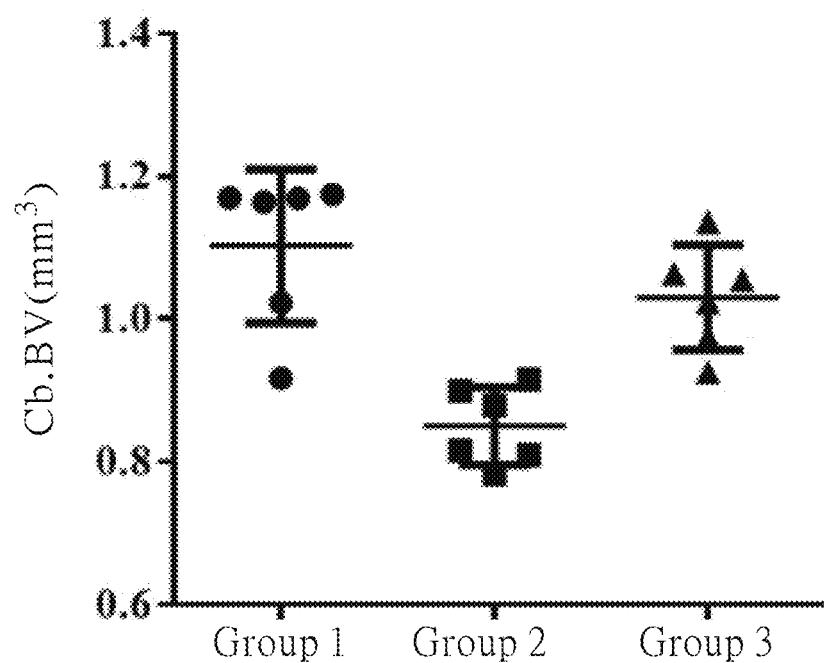
FIG. 27 shows the cortical bone volume of each group of mice.
Figure 28:
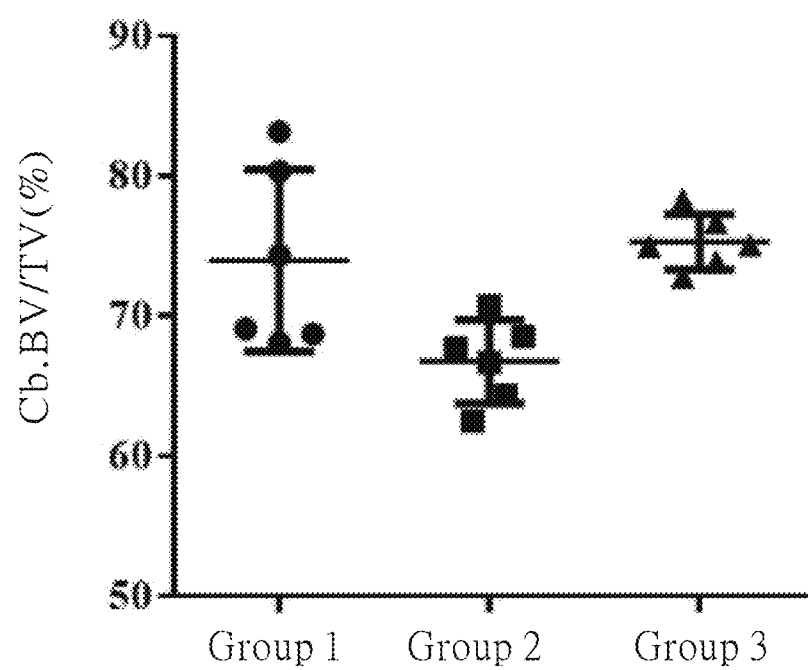
FIG. 28 shows the cortical bone volume-total volume ratio of each group of mice.
Figure 29:
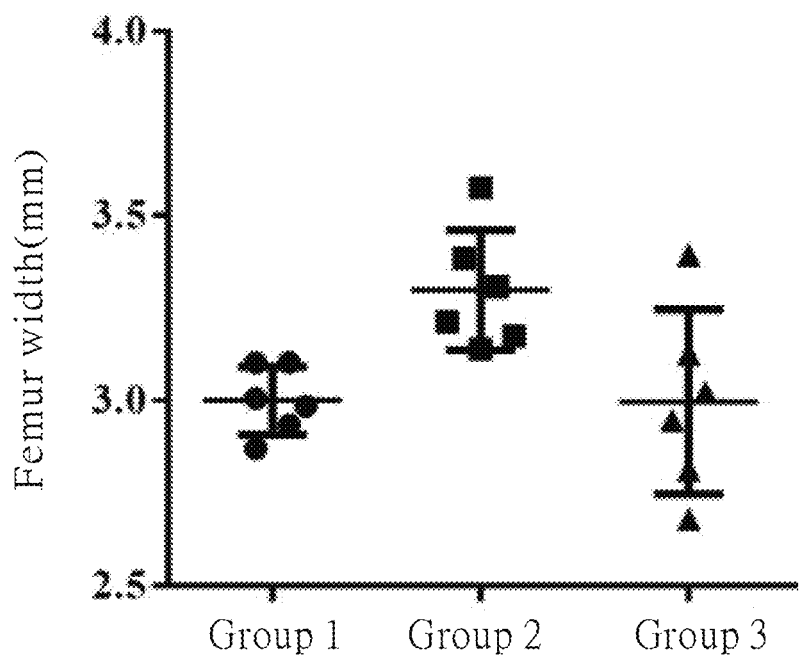
FIG. 29 shows the femur width of each group of mice.
Figure 30:
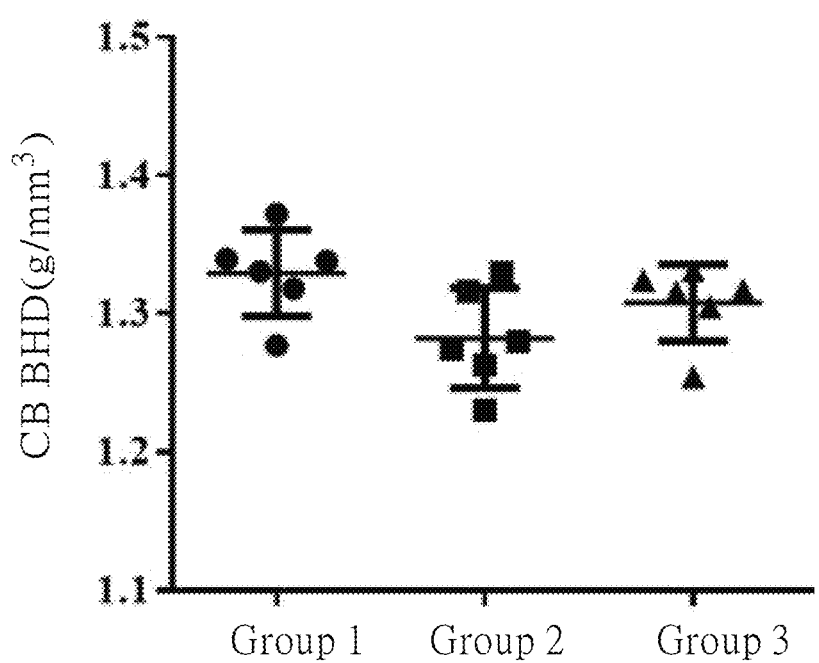
FIG. 30 shows the cortical bone mineral density of each group of mice.

Further, the ratio of RANKL to osteoprotegerin in the serum of each group of mice was calculated, as shown in FIG. 19.

Upon bone formation, the osteoblasts secrete P1NP and osteocalcin. When the contents of P1NP and osteocalcin are high, it indicates that the activity of osteoblasts is better. When the osteoclasts undergo bone resorption, many short peptides, such as CTX-1, are released in the blood. Therefore, when the CTX-1 content in the blood or femoral bone marrow effluent is high, it indicates that the osteoclasts have high activity. As can be known from the results shown in FIGS. 14 to 16, the P1NP and osteocalcin contents in the serum and bone marrow effluent of the second group of mice are lower than those in the first group of mice, and the CTX-1 content is higher than that in the first group of mice, so that the activity of the osteoblasts in the second group of mice is low, and the activity of the osteoclasts is high, indicating that the second group of mice are mice with osteoporosis. Compared with the second group of mice, the in-vivo P1NP and osteocalcin levels in the third group of mice are significantly elevated, and the CTX-1 content is significantly lowered, indicating that administration of the peptide of the present invention can increase the activity of osteoblasts, and inhibit the activation of osteoclasts.

Furthermore, RANKL is one of the cytokines required for differentiation and activation of osteoclasts. When osteoclasts act unduly, osteoblasts secrete osteoprotegerin to bind to RANKL, thereby inhibiting bone resorption. That is, when the RANKL content is high or/and the osteoprotegerin content is low, it indicates that an individual is at high risk of occurrence or deterioration of osteoporosis. As can be known from the results shown in FIGS. 17 to 19, compared with the first group of mice, the in-vivo RANKL content in the second group of mice is significantly increased, and the osteoprotegerin content is significantly decreased, showing an imbalance in the bone metabolism and rapid bone loss of the second group of mice. Compared with the second group of mice, the RANKL content in the third group of mice administered with the peptide of the present invention is significantly decreased, and a large amount of osteoprotegerin is secreted, showing that the bone metabolism of the third group of mice has a tendency toward bone regeneration.

Accordingly, as can be known from the results shown in FIGS. 14 to 19, administration of the peptide of SEQ ID No. 1 of the present invention can increase the bone synthesis indices and reduce the bone absorption indices in an individual, showing that the peptide of SEQ ID No. 1 of the present invention can promote the proliferation of osteoblasts and inhibit the functions of osteoclasts, whereby not only the deterioration of osteoporosis-related diseases can be avoided, but also the effect of treating or/and preventing osteoporosis-related conditions can be achieved by increasing the efficiency of bone formation.

Example 15: Analysis by Computed Tomography Scan

The bones of each group of mice in Example 9 were scanned with a computed tomography scanner (Micro-CT, Skyscan, Belgium), and 3D images were created with CTAn software and adjusted to obtain the changes in the structure of trabecular bone and cortical bone of each group of mice. Also, the trabecular bone volume-to-total volume ratio (Tb.BV/TV), average trabecular thickness (Tb.Th), trabecular number (Tb.N), trabecular spacing (Tb.Sp) trabecular bone mineral density (Tb.BMD), cortical bone volume (Cb.BV), cortical bone surface-area-to-bone-volume ratio (Cb.BS/BV), cortical bone volume-total volume ratio (Cb.BV/TV), femur width, and cortical bone mineral density (Cb.BMD) were calculated by the analysis function of the software. The results are shown in FIGS. 20 to 30.

As can be clearly known from the results shown in FIGS. 20 to 30, since the rate of bone loss in the second group of mice is greater than the rate of bone formation, the second group of mice have a loose bone structure, a small trabecular thickness, a reduced trabecular number, a high trabecular spacing, a low cortical bone surface-area-to-bone-volume ratio, a low bone mineral density, an increased cortical bone diameter, a lowered bone density, and poor support of cortical bone, compared with the first group of mice. Since the peptide disclosed in the present invention can shift the bone metabolism of the third group of mice toward the direction of bone formation, the results of computed tomography scan and analysis show that the bone structure and bone density of the third group of mice are significantly better than those of the second group of mice, and have no significant difference from those of the first group of mice.

It can be seen that the peptide of SEQ ID No. 1 of the present invention not only can improve or inhibit the bone loss, but also can effectively increase the bone density, showing that the peptide of SEQ ID No. 1 of the present invention has the ability to promote the proliferation and differentiation of osteoblasts, thus stimulating bone formation, and achieving the effect of preventing or/and treating osteoporosis-related conditions.

Figure 31A:
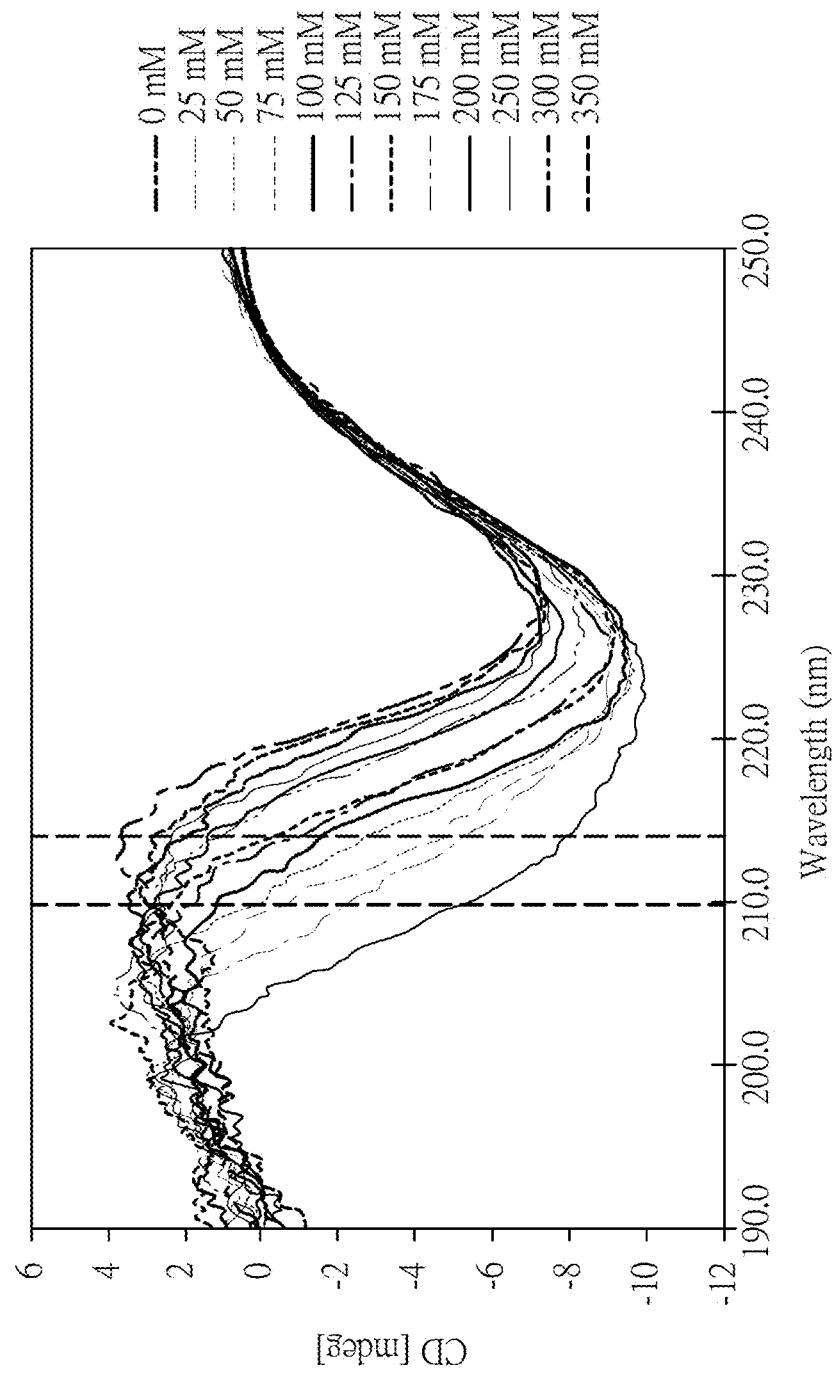
FIG. 31A shows the results analyzed by circular dichroism spectroscopy of the reaction of the peptide of SEQ ID NO. 1 according to the present invention with various concentrations of calcium ions.
Figure 31B:
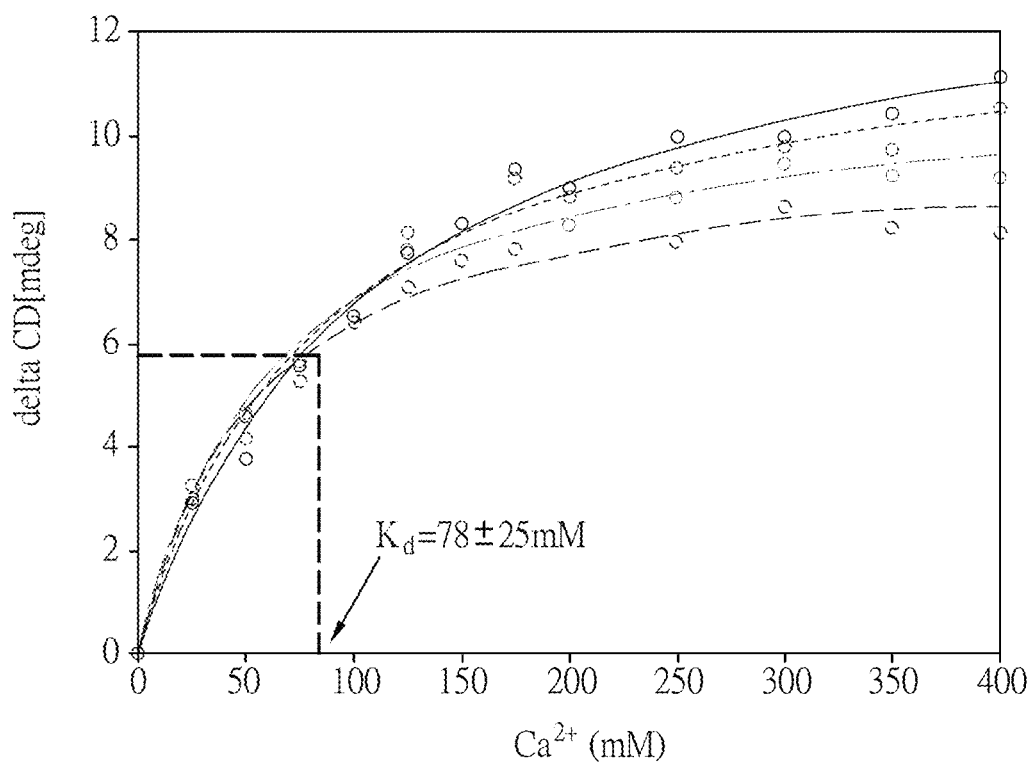
FIG. 31B shows the relationship between the circular dichroism spectral data of FIG. 31A and the calcium ion concentration.
Figure 32:
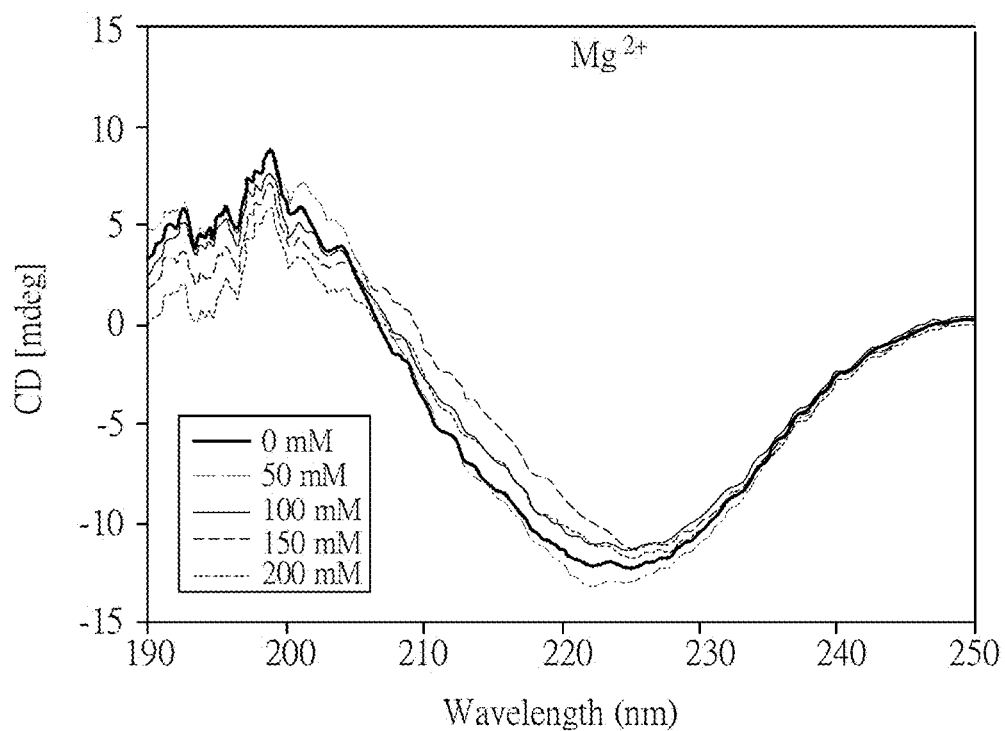
FIG. 32 shows the results analyzed by circular dichroism spectroscopy of the reaction of the peptide of SEQ ID NO. 1 according to the present invention with various concentrations of magnesium ions.
Figure 33:
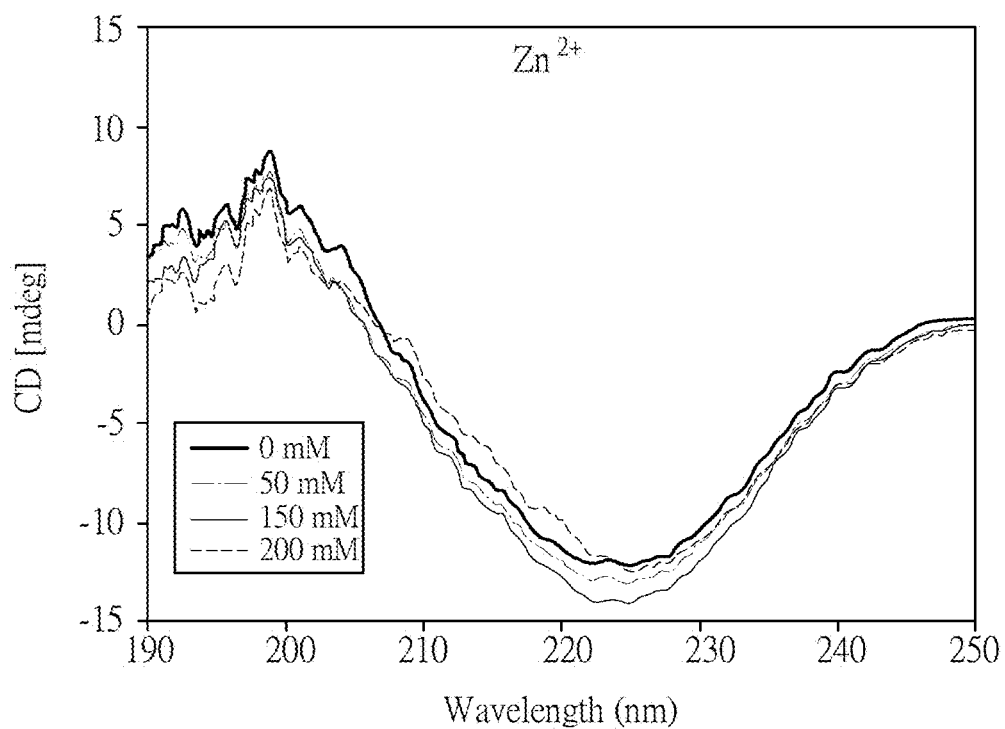
FIG. 33 shows the results analyzed by circular dichroism spectroscopy of the reaction of the peptide of SEQ ID NO. 1 according to the present invention with various concentrations of zinc ions.

Example 16: Analysis of the Binding of the Peptide of the Present Invention and Calcium Ions by Circular Dichroism (CD) Spectroscopy The peptide of SEQ ID No. 1 of the present invention was reacted with various concentrations of calcium ions, magnesium ions and zinc ions, respectively, and after the reaction, the ability of the peptide of SEQ ID No. 1 of the present invention to bind to different ions is analyzed by a circular dichroism spectroscopy. The results are shown in FIGS. 31 to 33. The results in FIGS. 31 to 33 show that the peptide of SEQ ID No. 1 of the present invention can specifically bind to calcium ions, and is unable to bind to magnesium or zinc ions.

Figure 34:
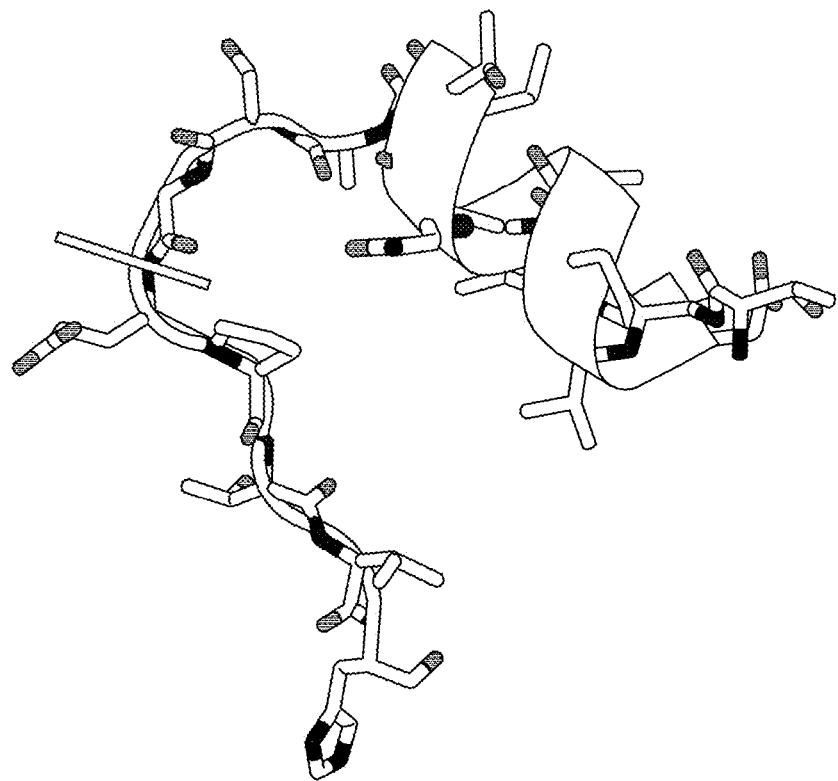
FIG. 34 is a view showing a simulated 3D structure of the peptide of SEQ ID NO. 1 disclosed in the present invention.
Figure 35:
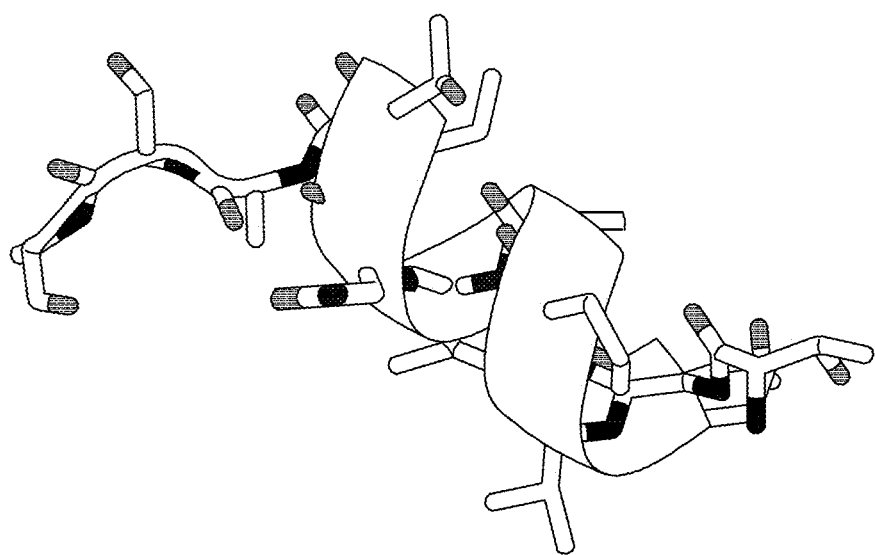
FIG. 35 is a view showing a simulated 3D structure of the peptide of SEQ ID NO. 2 disclosed in the present invention.

Example 17: Confirmation of the Active Fragment of the Peptide of the Present Invention According to previous results by spectroscopy, the 3D structure of the peptide of SEQ ID No. 1 of the present invention was simulated (as shown in FIG. 34), and the C-terminal 5 amino acids of the peptide of the present invention were removed, to obtain the peptide of SEQ ID No. 2, of which the 3D structure was simulated (as shown in FIG. 35). It can be seen from comparison of FIG. 34 and FIG. 35 that the peptides of SEQ ID No. 1 and SEQ ID No. 2 of the present invention both have a helical structure, and their sequences were compared and found that the helical structure is derived from a sequence consisting of the six amino acids: SEQ ID No. 3.

Further, with reference to the processes disclosed in Examples 1 and 2, whether the peptides of SEQ ID No. 1 and the peptide of SEQ ID No. 2 of the present invention have the ability to promote calcium absorption was detected. The results are as shown in FIG. 36, showing that the peptide of SEQ ID No. 2 and the peptide of SEQ ID No. 1 both have the ability to promote calcium absorption.

Figure 36:
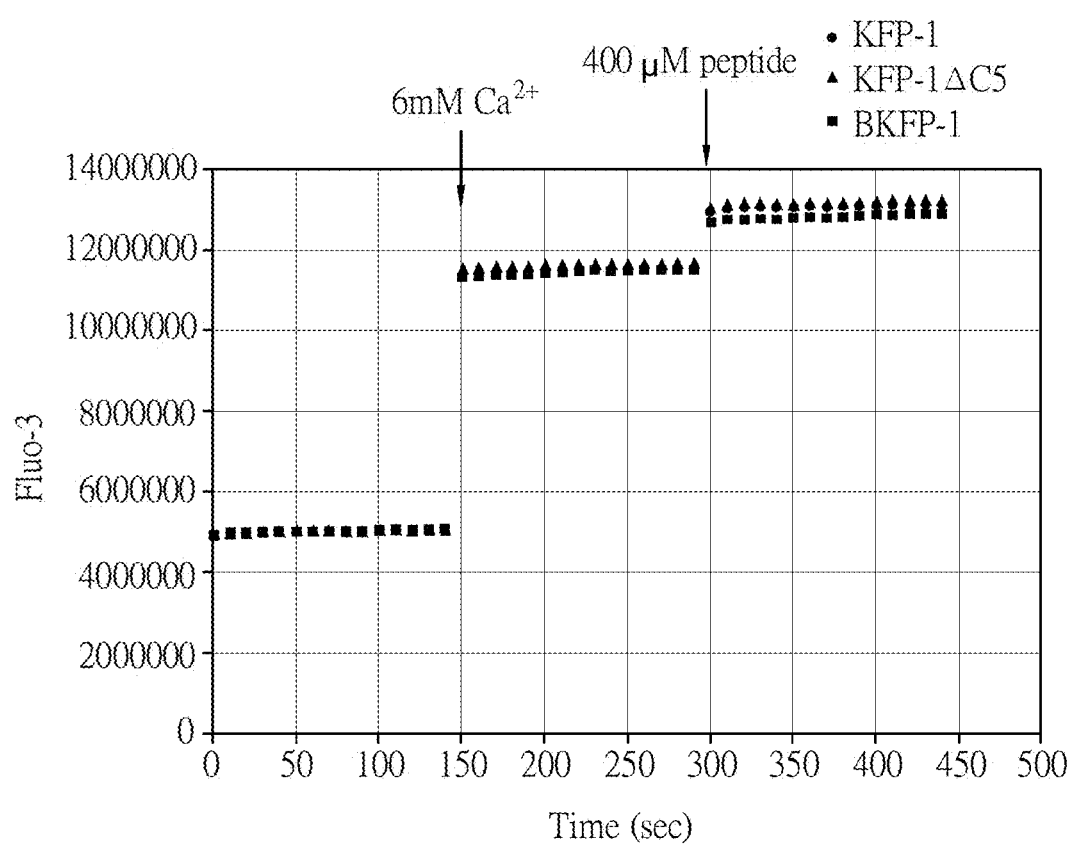
FIG. 36 shows the calcium-absorption promotion ability of the peptide of SEQ ID NO. 1 and the peptide of SEQ ID NO. 2 according to the present invention.

Therefore, it can be inferred from the results of FIGS. 34 to 36 that for the peptide fragment of SEQ ID No. 1, the peptide of SEQ ID No. 2 is a main functional fragment therein. Moreover, according to the structures of the peptide of SEQ ID No. 1 and the peptide of SEQ ID No. 2, it can be reasonably determined that the peptide fragment of SEQ ID No. 3 capable of forming the helical structure is the main portion responsible for binding to calcium ions. That is, the peptide fragment of SEQ ID No. 3 has the ability to prevent or treat osteoporosis-related diseases.

As can be seen from the above description, the novel peptide disclosed in the pre s ent invention can effectively transport calcium ions into cells via the calcium ion channel V6, and the efficiency of transporting calcium ions into cells increases with increasing dose of the novel peptide administered, thus achieving the effect of preventing or treating calcium ion deficiency-related diseases. Furthermore, the novel peptide disclosed in the present invention can reduce the levels of oxidative stress and inflammation-related cytokines in the cells, thereby inhibiting the proliferation of osteoclasts and the apoptosis of bone cells, promoting the proliferation and differentiation of osteoblasts, and thus increasing the osteoblast count. That is, the novel peptide disclosed in the present invention can enhance the efficiency of bone formation, to achieve the effect of treating or/and preventing osteoporosis-related diseases. In addition, the novel peptide disclosed in the present invention have the effect of treating or/and preventing inflammatory related diseases. Accordingly, the novel peptide disclosed in the present invention can be used as an active ingredient in a pharmaceutical composition or a component of a food to provide for different needs.

The present invention has been described in detail above with reference to examples. Simple modifications or changes can be made to the embodiments herein by those skilled in the art without departing from the spirit of the present invention, which all fall within the protection scope of the present invention as defined by the claims.

What is claimed is:

1. A method for treating osteoporosis in a subject in need thereof, comprising administering to the subject a composition containing an effective amount of a peptide set forth in the amino acid sequence of SEQ ID NO: 1 or SEQ ID NO: 2.

2. The method for treating osteoporosis according to claim 1, wherein the composition is a pharmaceutical composition.

3. The method for treating osteoporosis according to claim 1, wherein the composition is a nutritional supplement.

4. The method for treating osteoporosis according to claim 1, wherein the composition is a functional food.

5. The method for treating osteoporosis according to claim 1, wherein the subject suffers from an inflammatory disease.

6. The method for treating osteoporosis according to claim 1, wherein the composition inhibits bone loss.

7. The method for treating osteoporosis according to claim 1, wherein the composition promotes bone growth.

* * * * *